(12) United States Patent
Meggers et al.

(10) Patent No.: US 8,080,660 B2
(45) Date of Patent: *Dec. 20, 2011

(54) METAL COMPLEX GLYCOGEN SYNTHASE KINASE 3 INHIBITORS

(75) Inventors: Eric Meggers, Philadelphia, PA (US); Howard Bregman, Philadelphia, PA (US); Douglas S. Williams, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 1324 days.

This patent is subject to a terminal disclaimer.

(21) Appl. No.: 11/228,381

(22) Filed: Sep. 19, 2005

(65) Prior Publication Data

US 2006/0019942 A1    Jan. 26, 2006

Related U.S. Application Data

(63) Continuation of application No. 11/045,331, filed on Jan. 31, 2005, now Pat. No. 7,488,817.

(60) Provisional application No. 60/540,591, filed on Feb. 2, 2004, provisional application No. 60/610,607, filed on Sep. 17, 2004.

(51) Int. Cl.
*C07F 15/00* (2006.01)
(52) U.S. Cl. .......................................................... 546/2
(58) Field of Classification Search ................. 546/2
See application file for complete search history.

(56) References Cited

U.S. PATENT DOCUMENTS

| 6,451,838 | B1 | 9/2002 | Moon et al. |
| 6,555,539 | B2 | 4/2003 | Reich et al. |
| 6,593,357 | B1 | 7/2003 | Green et al. |
| 6,613,776 | B2 | 9/2003 | Knegtel et al. |
| 7,671,046 | B2 | 3/2010 | Meggers et al. |
| 2005/0171076 | A1* | 8/2005 | Meggers et al. .............. 514/185 |

OTHER PUBLICATIONS

West, Anthony R., Solid State Chemistry and its Applications, Wiley, New York, 1988, pp. 358 and 365.*

* cited by examiner

*Primary Examiner* — James O Wilson
*Assistant Examiner* — Brian McDowell
(74) *Attorney, Agent, or Firm* — Woodcock Washburn, LLP

(57) ABSTRACT

The present inventive subject matter relates to novel metal complex glycogen synthase kinase 3 inhibitors, methods for making such compounds, and methods for using such compounds for treating diseases and disorders mediated by glycogen synthase kinase 3 activity. Compound II, below, represents an exemplary metal complex glycogen synthase kinase 3 inhibitor according to the present disclosure, wherein variable groups are defined as provided herein:

(II)

2 Claims, 5 Drawing Sheets (ATP and Staurosporine (1) are prior art compounds)

METAL COMPLEX GLYCOGEN SYNTHASE KINASE 3 INHIBITORS

This application is a continuation-in-part of U.S. patent application Ser. No. 11/045,331, filed Jan. 31, 2005 now U.S. Pat. No. 7,488,817, which claims the benefit of U.S. Provisional Patent Application No.60/540,591, filed Feb. 2, 2004, the contents of which are hereby incorporated by reference in their entirety; this application further claims the benefit of U.S. Provisional Patent Application No.60/610,607, filed Sep. 17, 2004, the contents of which is hereby incorporated by reference in its entirety.

BACKGROUND OF THE INVENTION

1. Field of the Invention

The present invention relates to novel metal complex glycogen synthase kinase 3 inhibitors, methods for making such compounds, and methods for using such compounds for treating diseases and disorders mediated by glycogen synthase kinase 3 activity.

2. Description of the Background

The development of high affinity and specific compounds for a given protein target is a great and often unsolved challenge. For example, the human genome codes for more than 500 protein kinases and many of them constitute major drug targets since mutations and dysregulations in protein kinases play important roles in disease. Yet, not a single existing kinase inhibitor is completely specific for a particular kinase. The development of small molecules that perturb specific protein functions is of great importance for probing biological processes and ultimately for the development of potent and safe drugs.

Medicinal chemistry is predominately focused on organic chemistry. In the cases where metals are employed, it is for their reactivity and or imaging properties (see FIG. 1). Applicant explores a different direction and bridges the fields of organic and inorganic medicinal chemistry by using metal centers as chemically inert structural scaffolds for drug design. Such metal-ligand assemblies allow convergent and economical synthetic approaches and give access to structural motifs that differ from purely organic molecules.

Further, medicinal chemistry is predominately focused on the design of organic molecules, whereas the incorporation of inorganic components into drugs is much less investigated. Furthermore, in almost all metallopharmaceuticals, the metal ion possesses a reactive feature. We have found that certain organometallic and inorganic compounds are useful as structural scaffolds for enzyme inhibition. Such metal-ligand assemblies allow convergent synthetic approaches and give access to structural motifs that differ from purely organic molecules. Nature makes extended use of metals not only for their reactivity but also for structural purposes, as for example in zinc binding aspartate transcarbamoylase and zinc finger domains, or the calcium binding protein calmodulin.

Protein kinases regulate most aspects of cellular life and are one of the main drug targets. An example is the microbial alkaloid staurosporine, which is a very potent, but relatively nonspecific inhibitor of many protein kinases. Many staurosporine derivatives and related organic compounds with modulated specificities have been developed and several are in clinical trials as anticancer drugs. They all share an indolo [2,3-α]carbazole aglycon which binds to the ATP binding site and can hydrogen bond with two conserved amino acids. For this class of inhibitors, specificity for a particular protein kinase can be achieved by the moiety which is attached to the indole nitrogen atoms.

Glycogen synthase kinase 3 (GSK3) is a serine/threonine kinase for which two isoforms, α and β, have been identified. Woodgett, Trends Biochem. Sci., 16:177-81 (1991). Both GSK3 isoforms are constitutively active in resting cells. GSK3 was originally identified as a kinase that inhibits glycogen synthase by direct phosphorylation. Upon insulin activation, GSK3 is inactivated, thereby allowing the activation of glycogen synthase and possibly other insulin-dependent events, such glucose transport. Subsequently, it has been shown that GSK3 activity is also inactivated by other growth factors that, like insulin, signal through receptor tyrosine kinases (RTKs). Examples of such signaling molecules include IGF-1 and EGF. Saito et al., Biochem J., 303:27-31 (1994); Welsh et al., Biochem. J.294:625-29 (1993); and Cross et al., Biochem. J., 303:21-26 (1994).

Despite the apparent promise of glycogen synthase kinase 3 modulators as a target for controlling disorders, very few of such compounds appear in the patent database. Examples of these are pyrazole compositions useful as glycogen synthase kinase 3 inhibitors, especially as inhibitors of aurora-2 and GSK-3, for treating diseases such as cancer, diabetes, and Alzheimer's disease. Another example is that of pyrazine based inhibitors of glycogen synthase kinase 3, for treating diseases such as diabetes, Alzheimer's disease and other neurodegenerative disorders, obesity, atherosclerotic cardiovascular disease, essential hypertension, polycystic ovary syndrome, syndrome X, ischemia, traumatic brain injury, bipolar disorder, immunodeficiency or cancer.

Thus, there is a significant need in the art for more specific and effective glycogen synthase kinase 3 inhibitors, which can be targeted to specific tissues and/or disease states. Applicants have developed metal complexes that target the ATP binding site of glycogen synthase kinase 3. Additional ligands in the coordination sphere of the metal ion undergo additional specific contacts with other parts of the active site, giving metal complex binders with high affinity and specificity for glycogen synthase kinase 3.

SUMMARY OF THE INVENTION

The present invention relates to a compound of the chemical formula

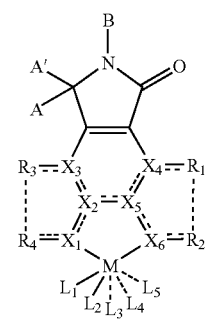

I or a pharmaceutically acceptable salt, ester, or solvate thereof, wherein:

each $X_1$, $X_2$, $X_3$, $X_4$, $X_5$ and $X_6$, independently, comprises N, C, S, O, B or Si;

each $R_1$, $R_2$, $R_3$ and $R_4$, independently, comprises 1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, $(C_1\text{-}C_9)$alkoxy, $(C_2\text{-}C_9)$alkenyloxy, $(C_3\text{-}C_8)$cycloalkyl, $(C_5\text{-}C_7)$cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched $(C_1\text{-}C_9)$alkyl, straight or branched $(C_1\text{-}$ $C_9$)alkyl substituted with one or more halo, trifluoromethyl, nitro, straight or branched ($C_1$-$C_6$)alkyl, straight or branched ($C_2$-$C_6$)alkenyl, hydroxy, ($C_1$-$C_4$)alkoxy, ($C_2$-$C_4$)alkenyloxy, phenoxy, benzyloxy, amino, or aryl (Ar), O—(($C_1$-$C_9$)alkyl), which may be straight or branched, straight or branched ($C_2$-$C_9$)alkenyl or alkynyl, and straight or branched ($C_2$-$C_9$)alkenyl or alkynyl substituted with one or more halo, trifluoromethyl, nitro, straight or branched ($C_1$-$C_6$)alkyl, straight or branched ($C_2$-$C_6$)alkenyl, hydroxy, ($C_1$-$C_4$)alkoxy, ($C_2$-$C_4$)alkenyloxy, phenoxy, benzyloxy, amino, or Ar, O—(($C_2$-$C_9$)alkenyl), which may be straight or branched, or Ar, and/or $R_1$ and $R_2$, which taken together form a mono-, bi- or tricyclic, carbo- or heterocyclic substituted or unsubstituted ring, wherein when the ring is monocyclic it comprises a 5 to 7 atom ring, when bicyclic or tricyclic it comprises a 3 to 8 atom ring, and when heterocyclic it comprises 1 to 5 O, N and/or S heteroatomic ring, and/or $R_3$ and $R_4$, which taken together form a mono-, bi- or tricyclic, carbo- or heterocyclic substituted or unsubstituted ring, wherein when the ring is monocyclic it comprises a 5 to 7 member ring, when bicyclic or tricyclic it comprises a 3 to 8 member ring, and when heterocyclic it comprises a 1-5 O, N and/or S heteroatomic ring;

Ar comprises a mono-, bi- or tricyclic, carbo- or heterocyclic ring that may be either unsubstituted or substituted in one or more position(s) with halo, hydroxyl, nitro, trifluoromethyl, straight or branched ($C_1$-$C_6$) alkyl or alkenyl, ($C_1$-$C_4$) alkoxy, ($C_1$-$C_4$)alkenyloxy, phenoxy, benzyloxy, or amino; wherein when the ring is a monocyclic ring it comprises a 5-7 membered ring, when a bicyclic or tricyclic ring it comprises a 3-8 membered ring, and when heterocyclic it comprises a 1-5 O, N and/or S heteroatomic ring;

M comprises Ru, Pt, Tc, Re, Os, Rh, Ir, Pd, Au, Cu or any other metal or half-metal; each A and A', independently, comprises hydrogen, hydroxy, hydroxymethyl, straight or branched ($C_1$-$C_6$) chain alkyl, straight or branched ($C_2$-$C_6$) alkenyl, O-(straight or branched ($C_1$-$C_6$)alkyl), and O-(straight or branched ($C_2$-$C_6$)alkenyl), or A and A' are taken together as =O;

B is hydrogen or $C_1$-$C_6$ straight or branched chain alkyl; and each $L_1$ to $L_n$, independently, comprise a monodentate ligand capable of acting as a ligand for M, and/or $L_1$ and $L_2$, taken together, comprise a bidentate ligand capable of acting as a ligand for M, and/or $L_1$, $L_2$ and $L_3$, taken together, comprise a tridentate ligand capable of acting as a ligand for M, and/or $L_1$, $L_2$, $L_3$ and $L_4$, taken together, comprise a tetradentate ligand capable of acting as a ligand for M; and n comprises a 2, 3, 4 or 5 integer.

The present invention also relates to a method for modulating glycogen synthase kinase 3 activity in a subject in need thereof, which comprises administering to a subject (human or animal) an effective amount of a compound of the chemical formula

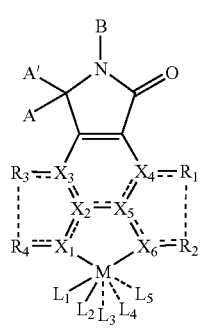

I or a pharmaceutically acceptable salt, ester, or solvate thereof, wherein each $X_1$, $X_2$, $X_3$, $X_4$, $X_5$ and $X_6$ independently, comprises N, C, S, O, B or Si;

each $R_1$, $R_2$, $R_3$ and $R_4$, independently, comprises 1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, ($C_1$-$C_9$)alkoxy, ($C_2$-$C_9$)alkenyloxy, ($C_3$-$C_8$)cycloalkyl, ($C_5$-$C_7$)cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched ($C_1$-$C_9$)alkyl, straight or branched ($C_1$-$C_9$)alkyl substituted with one or more halo, trifluoromethyl, nitro, straight or branched ($C_1$-$C_6$)alkyl, straight or branched ($C_2$-$C_6$)alkenyl, hydroxy, ($C_1$-$C_4$)alkoxy, ($C_2$-$C_4$)alkenyloxy, phenoxy, benzyloxy, amino, or aryl (Ar), O—(($C_1$-$C_9$)alkyl), which may be straight or branched, straight or branched ($C_2$-$C_9$)alkenyl or alkynyl, and straight or branched ($C_2$-$C_9$)alkenyl or alkynyl substituted with one or more halo, trifluoromethyl, nitro, straight or branched ($C_1$-$C_6$)alkyl, straight or branched ($C_2$-$C_6$)alkenyl, hydroxy, ($C_1$-$C_4$)alkoxy, ($C_2$-$C_4$) alkenyloxy, phenoxy, benzyloxy, amino, or Ar, O—(($C_2$-$C_9$) alkenyl), which may be straight or branched, or Ar, and/or $R_1$ and $R_2$, which taken together form a mono-, bi- or tricyclic, carbo- or heterocyclic substituted or unsubstituted ring, wherein when the ring is monocyclic it comprises a 5 to 7 atom ring, when bicyclic or tricyclic it comprises a 3 to 8 atom ring, and when heterocyclic it comprises 1 to 5 O, N and/or S heteroatomic ring, and/or $R_3$ and $R_4$, which taken together form a mono-, bi- or tricyclic, carbo- or heterocyclic substituted or unsubstituted ring, wherein when the ring is monocyclic it comprises a 5 to 7 member ring, when bicyclic or tricyclic it comprises a 3 to 8 member ring, and when heterocyclic it comprises a 1-5 O, N and/or S heteroatomic ring;

Ar comprises a mono-, bi- or tricyclic, carbo- or heterocyclic ring that may be either unsubstituted or substituted in one or more position(s) with halo, hydroxyl, nitro, trifluoromethyl, straight or branched ($C_1$-$C_6$)alkyl or alkenyl, ($C_1$-$C_4$) alkoxy, ($C_1$-$C_4$)alkenyloxy, phenoxy, benzyloxy, or amino; wherein when the ring is a monocyclic ring it comprises a 5-7 membered ring, when a bicyclic or tricyclic ring it comprises a 3-8 membered ring, and when heterocyclic it comprises a 1-5 O, N and/or S heteroatomic ring;

M comprises Ru, Pt, Tc, Re, Os, Rh, Ir, Pd, Au, Cu or any other metal or half-metal;

each A and A', independently, comprises hydrogen, hydroxy, hydroxymethyl, straight or branched ($C_1$-$C_6$) chain alkyl, straight or branched ($C_2$-$C_6$)alkenyl, O-(straight or branched ($C_1$-$C_6$)alkyl), and O-(straight or branched ($C_2$-$C_6$) alkenyl), or A and A' are taken together as =O;

B is hydrogen or $C_1$-$C_6$ straight or branched chain alkyl; and each $L_1$ to $L_n$, independently, comprise a monodentate ligand capable of acting as a ligand for M, and/or $L_1$ and $L_2$, taken together, comprise a bidentate ligand capable of acting as a ligand for M, and/or $L_1$, $L_2$ and $L_3$, taken together, comprise a tridentate ligand capable of acting as a ligand for M, and/or $L_1$, $L_2$, $L_3$ and $L_4$, taken together, comprise a tetradentate ligand capable of acting as a ligand for M; and n comprises a 2, 3, 4 or 5 integer.

The present invention also relates to a pharmaceutical composition comprising a therapeutically effective amount of the compound of the chemical formula

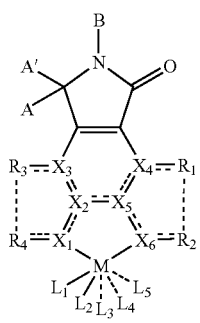

or pharmaceutically acceptable salt, ester, or solvate thereof, wherein each $X_1$, $X_2$, $X_3$, $X_4$, $X_5$ and $X_6$, independently, comprises N, C, S, O, B or Si;

each $R_1$, $R_2$, $R_3$ and $R_4$, independently, comprises 1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, ($C_1$-$C_9$)alkyl, ($C_2$-$C_9$)alkenyloxy, ($C_3$-$C_8$)cycloalkyl, ($C_5$-$C_7$)cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched ($C_1$-$C_9$)alkyl, straight or branched ($C_1$-$C_9$)alkyl substituted with one or more halo, trifluoromethyl, nitro, straight or branched ($C_1$-$C_6$)alkyl, straight or branched ($C_2$-$C_6$)alkenyl, hydroxy, ($C_1$-$C_4$)alkoxy, ($C_2$-$C_4$)alkenyloxy, phenoxy, benzyloxy, amino, or aryl (Ar), O—(($C_1$-$C_9$)alkyl), which may be straight or branched, straight or branched ($C_2$-$C_9$)alkenyl or alkynyl, and straight or branched ($C_2$-$C_9$)alkenyl or alkynyl substituted with one or more halo, trifluoromethyl, nitro, straight or branched ($C_1$-$C_6$)alkyl, straight or branched ($C_2$-$C_6$)alkenyl, hydroxy, ($C_1$-$C_4$)alkoxy, ($C_2$-$C_4$)alkenyloxy, phenoxy, benzyloxy, amino, or Ar, O—(($C_2$-$C_9$)alkenyl), which may be straight or branched, or Ar, and/or $R_1$ and $R_2$, which taken together form a mono-, bi- or tricyclic, carbo- or heterocyclic substituted or unsubstituted ring, wherein when the ring is monocyclic it comprises a 5 to 7 atom ring, when bicyclic or tricyclic it comprises a 3 to 8 atom ring, and when heterocyclic it comprises I to 5 O, N and/or S heteroatomic ring, and/or $R_3$ and $R_4$, which taken together form a mono-, bi- or tricyclic, carbo- or heterocyclic substituted or unsubstituted ring, wherein when the ring is monocyclic it comprises a 5 to 7 member ring, when bicyclic or tricyclic it comprises a 3 to 8 member ring, and when heterocyclic it comprises a 1-5 O, N and/or S heteroatomic ring;

Ar comprises a mono-, bi- or tricyclic, carbo- or heterocyclic ring that may be either unsubstituted or substituted in one or more position(s) with halo, hydroxyl, nitro, trifluoromethyl, straight or branched ($C_1$-$C_6$)alkyl or alkenyl, ($C_1$-$C_4$) alkoxy, ($C_1$-$C_4$)alkenyloxy, phenoxy, benzyloxy, or amino; wherein when the ring is a monocyclic ring it comprises a 5-7 membered ring, when a bicyclic or tricyclic ring it comprises a 3-8 membered ring, and when heterocyclic it comprises a 1-5 O, N and/or S heteroatomic ring;

M comprises Ru, Pt, Tc, Re, Os, Rh, Ir, Pd, Au, Cu or any other metal or half-metal;

each A and A', independently, comprises hydrogen, hydroxy, hydroxymethyl, straight or branched ($C_1$-$C_6$) chain alkyl, straight or branched ($C_2$-$C_6$)alkenyl, O-(straight or branched ($C_1$-$C_6$)alkyl), and O-(straight or branched ($C_2$-$C_6$) alkenyl), or A and A' are taken together as =O;

B is hydrogen or $C_1$-$C_6$ straight or branched chain alkyl; and each $L_1$ to $L_n$, independently, comprise a monodentate ligand capable of acting as a ligand for M, and/or $L_1$ and $L_2$, taken together, comprise a bidentate ligand capable of acting as a ligand for M, and/or $L_1$, $L_2$ and $L_3$, taken together, comprise a tridentate ligand capable of acting as a ligand for M, and/or $L_1$, $L_2$, $L_3$ and $L_4$, taken together, comprise a tetradentate ligand capable of acting as a ligand for M; and n comprises a 2, 3, 4 or 5 integer; and (ii) a pharmaceutically acceptable carrier.

DETAILED DESCRIPTION OF THE PREFERRED EMBODIMENTS

Figure 1:
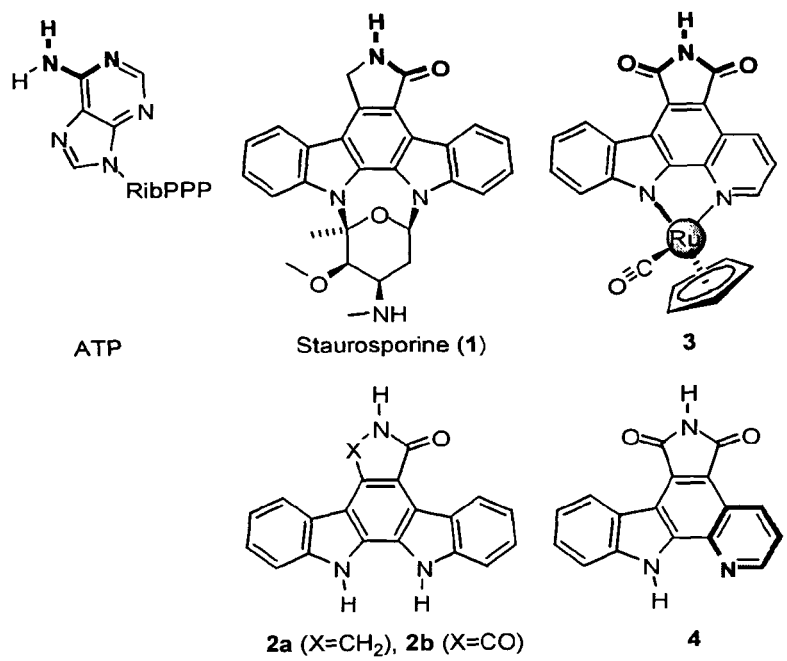
FIG. 1 depicts inventive and prior art compounds.
Figure 2:
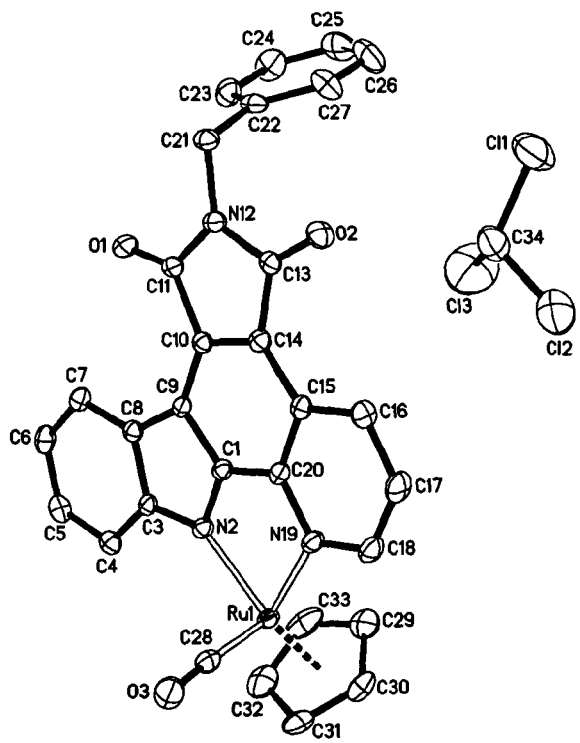
FIG. 2 shows the X-ray structure of the N-benzylated derivative of compound 3.

This invention arose from the desire of the inventor to improve over the prior art in terms of modulators of important enzymes such as glycogen synthase kinase 3. In the research leading to this work, the inventor discovered novel metal complex glycogen synthase kinase 3 inhibitors suitable for the intended purpose. The inventor further discovered novel and unobvious methods for making such inhibitor compounds, and methods for employing them in the treatment of diseases and disorders mediated by glycogen synthase kinase 3 activity.

DEFINITIONS

The term "therapeutically effective amount" as used herein refers to that amount of a compound which will contribute to the cancer-treating ability of the composition.

The term "treating" as used herein refers to partial or total inhibition of a disease state, disease progression, or disorder.

The term "preventing" as used herein refers to either preventing the onset of clinically evident disease or disorder altogether, or preventing the onset of a preclinically evident stage of a disease or disorder in individuals at risk.

The term "modulating" as used herein refers to the process of activating or inhibiting an activity, particularly the activity of a protein such as an enzyme.

The term "enhancing" the biological activity, function, health, or condition of an organism refers to the process of augmenting, fortifying, strengthening, or improving.

The term "isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

The term "pharmaceutically acceptable salt, ester, or solvate" refers to a salt, ester, or solvate of a subject compound which possesses the desired pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, the basic nitrogen-containing groups can be quarternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

The term "ligand" as used herein refers to any group which can form a coordination complex with a metal. A ligand offering one group for attachment to the metal is termed monodentate; two groups, bidentate; three or more groups, polydentate. A ligand may attach to the metal atom by covalent or ionic bond(s). Many compounds, too numerous to fully enumerate here, can act as ligands; common ligands include, but are not limited to, derivatives of amines (e.g. ethylenediamine), aldehydes and ketones, carboxylic acids (e.g. ethylenediaminetetraacetic acid (EDTA)), sulfonyl- and mercapto-derivative groups, phosphoryls and other phorphorus derivatives, hydroxamic acid derivatives, and various combinations thereof. Other examples of useful metal ligands include, without limitation, mercapto derivatives, hydroxamic acid derivatives, phosphorus derivatives (particularly those of the general formula X—P(O)(OH)—R, wherein R is as defined above for $R_1$), carboxyl derivatives, N-carboxyalkyl derivatives, aldehydes, ketones, and combinations thereof. In particular, useful ligands include, without limitation, derivatives of dicarboxylic acids, β-diketones, α-hydroxycarboxylic acids, alkyl and aryl diamines, α- and β-aminocarboxylates (including amino acid derivatives), thioethers, xanthates, dithiocarbamates, dithiocarboxylates, thioglycolates, thiols, and diphosphines.

The term "monodentate ligand" as used herein refers to an atom or compound which has one lone pair of electrons by which it can attach to another atom or compound. For example, many simple anions, or Lewis bases, can act as monodentate ligands, including, without limitation, chloride ion, hydroxide ion, water, and ammonia.

The term "bidentate ligand" as used herein refers to an atom or compound which has two lone pairs of electrons by which it can attach to another atom or compound. Similarly, the terms "tridentate ligand" and "tetradentate ligand" as used herein refer to an atom or compound which has, respectively, three and four lone pairs of electrons by which it can attach to another atom or compound.

The Inventive Compounds

The present invention provides novel and unobvious compounds of the chemical formula I. The development of small molecules that perturb specific protein functions is of great importance for probing biological processes and ultimately for the development of potent and safe drugs. Medicinal chemistry is predominately focused on the design of organic molecules, whereas the incorporation of inorganic components into drugs is much less investigated. Furthermore, in almost all metallopharmaceuticals, the metal ion possesses a reactive feature. We have found that certain organometallic and inorganic compounds are useful as structural scaffolds for enzyme inhibition. Such metal-ligand assemblies allow convergent synthetic approaches and give access to structural motifs that differ from purely organic molecules.

The vast majority of specific enzyme inhibitors are small organic molecules which gain their specificity by a combination of weak interactions including hydrogen bonding, electrostatic contacts, and hydrophobic interactions. In contrast, inorganic compounds find applications in medicinal chemistry predominately for their reactivity and their imaging properties. We started a research program that aims in exploring the versatility of organometallic and inorganic compounds as structural scaffolds for the design of specific enzyme inhibitors. It is noteworthy that coordinative bonds with transition metals such as ruthenium can reach kinetic stabilities that are comparable with those of covalent bonds. With this in mind, a ruthenium center may be considered as a virtual "hypervalent carbon" with unique structural opportunities.

The inventor introduced a strategy for developing ruthenium complexes that target the ATP-binding site of protein kinases by mimicking structural features of small organic molecule inhibitors. The adenine base of ATP is lined with a cleft-forming set of conserved hydrophobic residues and undergoes two hydrogen bonds to the backbone of the hinge between the N-terminal and C-terminal domain. Small molecule inhibitors usually copy this binding mode. For example, the protein kinase inhibitor staurosporine 1 contains the planar hydrophobic indolo[2,3-a]carbazole aglycon 2a in which the lactam moiety mimics the hydrogen bonding pattern of the adenine base. See FIG. 1.

The inventor envisioned that by replacing the indolocarbazole alkaloid scaffold with metal complexes in which the structural features of the indolocarbazole aglycon 2a or the related arcyriaflavin A 2b is retained in one of the ligands, the thus obtained metal complexes could be targeted to the ATP-binding site of protein kinases. In this manner, potent and specific inhibitors for a particular kinase were obtained by assembling elaborate structures around the metal center. The organometallic ruthenium compound 3 disclosed and claimed in this patent is an extremely potent example of the invention and a selective inhibitor for the glycogen synthase kinase 3 (GSK-3) enzyme.

The key component of the present design is the novel pyridocarbazole ligand 4, derived from arcyriaflavin A 2b by just replacing one indole moiety with a pyridine. See, FIG. 1, portion shown in red. The x-ray structure of the N-benzylated derivative of 3 proved that ligand 4 in fact serves as a bidentate ligand for ruthenium, having one classical coordinative bond with the pyridine (Ru1-N19=2.13 Å) in addition to one covalent s-bond with the indole nitrogen (Ru1-N2=2.11 Å) (indicated in green in FIG. 1). The coordination sphere is further filled up by a cyclopentadienyl and CO group. This neutral half-sandwich ruthenium complex 3 is stable under air, in water, and can even withstand the presence of millimolar concentrations of thiols as determined by 1H-NMR spectroscopy.

Figure 3:
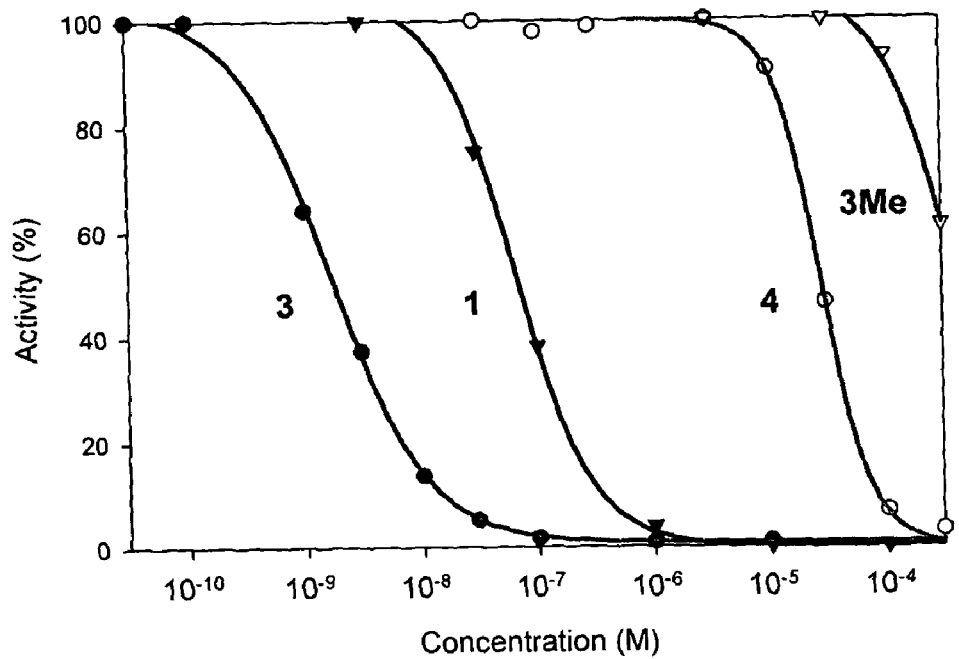
FIG. 3 depicts $IC_{50}$ curves with GSK-3α obtained by phosphorylation of a substrate with [λ-$^{32}$P]ATP. Curve 3: racemic complex 3 ($IC_{50}$=3 nM); Curve 1: staurosporine 1 ($IC_{50}$=50 nM); Curve 4: pyridocarbazole 4 ($IC_{50}$=50 μM); Curve 3Me: 3Me, the N-methylated derivative of 3 ($IC_{50}$>300 μM).

Screening of a small library of ruthenium complexes against a panel of protein kinases allowed the identification of compound 3 as an extremely potent inhibitor for the GSK-3 enzyme. The concentration at which 50% of the enzyme is inhibited ($IC_{50}$) is 3 nM for GSK-3α (α-isoform) and 10 nM for GSK-3β (β-isoform). We have not found any other protein kinase that is inhibited by 3 with such a potency. For example, Abl ($IC_{50}$=5 µM), CDK2/Cyclin A ($IC_{50}$=3 µM), CHK1 ($IC_{50}$=25 µM), Lck ($IC_{50}$=3 µM), MAPK1/Erk1 ($IC_{50}$>100 µM), PKCα (100 µM), c-Src (4 µM), and ZAP-70 ($IC_{50}$=15 µM) all yield micromolar inhibition. Only RSK1 shows a submicromolar inhibition with an $IC_{50}$ of 100 nM. The $IC_{50}$ curves of the racemic mixture of 3 and the corresponding pyridocarbazole ligand 4 against GSK-3α are shown in FIG. 3. See, red and green curves, respectively. The pyridocarbazole ligand 4, itself, is a very weak inhibitor for GSK-3 with an $IC_{50}$ of only 50 µM. This means that upon formation of the metal complex 3 the potency increases by a factor of more than 15,000. Consequently, the activity of complex 3 requires the entire assembly, kept together by the central ruthenium atom.

Figure 4:
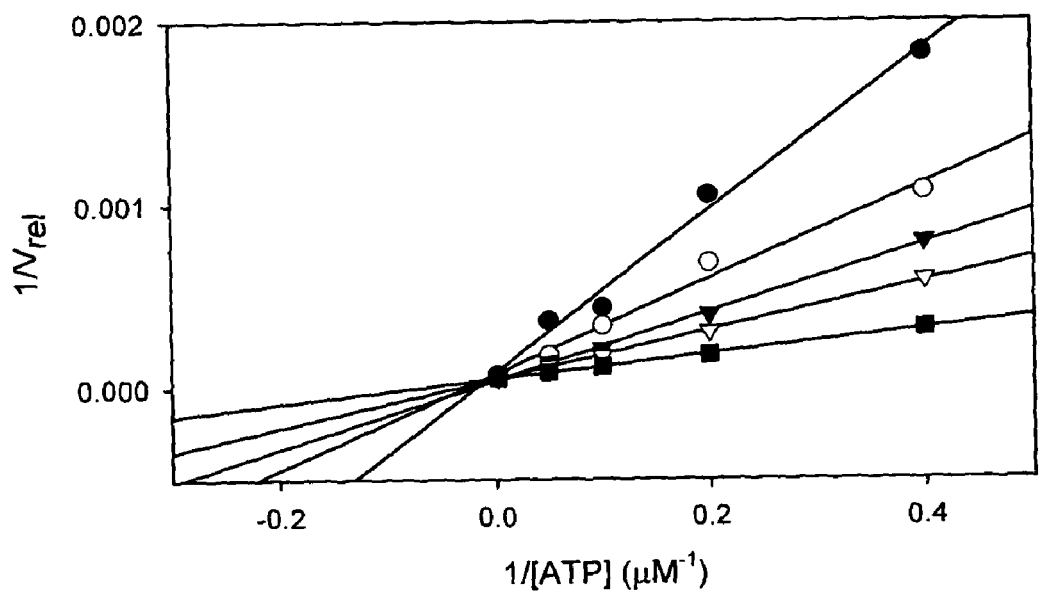
FIG. 4 depicts double-reciprocal plots of relative initial velocities (Vrel) against varying ATP concentrations in the presence of varying concentrations of compound 3.

In order to demonstrate that 3 does, as designed, bind to the ATP site, the inventor synthesized a derivative of compound 3 with the imide hydrogen replaced by a methyl group (3Me). This methylation abolishes the activity completely ($IC_{50}$>300 µM, see pink curve in FIG. 3), consistent with the assumption that the imide hydrogen is involved in hydrogen bonding with the adenine binding cleft. Additionally, a Lineweaver-Burk analysis (FIG. 4) of relative initial velocities of GSK-3α at different concentrations of ATP and 3 reaffirms ATP competitive binding and yields an inhibition constant ($K_i$) of 0.98±0.1 nM.

Figure 5A:
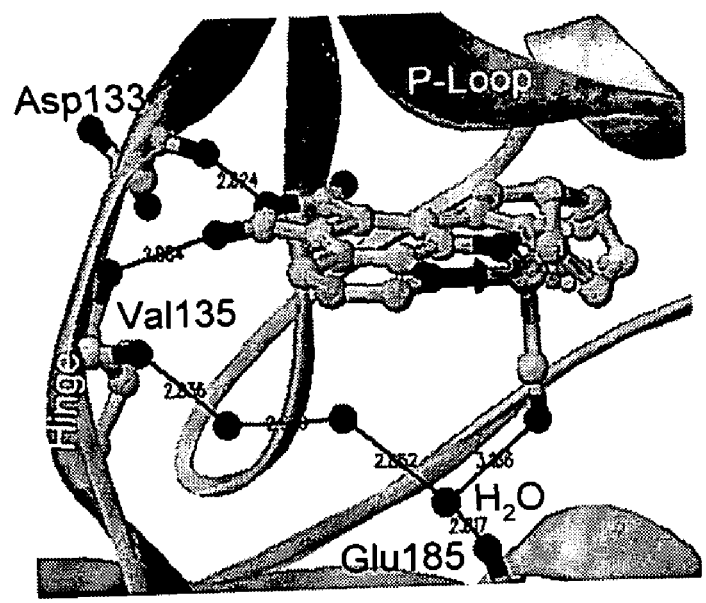
FIG. 5A depicts molecular modeling of interactions of 3-$R_{Ru}$ with the ATP binding site of GSK-3β.
Figure 5B:
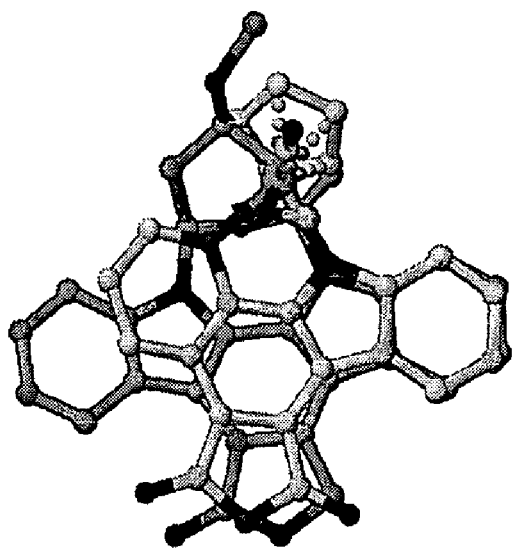
FIG. 5B depicts molecular modeling of the cocrystallized position of staurosporine in GSK-3β with the docked position of 3-$R_{Ru}$.

Ruthenium complex 3 is pseudo-tetrahedral and possesses metal-centered chirality. Interestingly, the activities of the individual enantiomers differ only twofold ($IC_{50}$=2 nM and 4 nM). In order to gain insight into the binding mode of 3 within the ATP-binding site of GSK-3, we modeled 3 into the active site of a cocrystallized structure of GSK-3(with staurosporine. It is likely that both enantiomers bind similarly due to their symmetrical imide group which allows for the same orientation of the CO and cyclopentadienyl ligands in the active site just by rotation of 180° around the pyridocarbazole. FIG. 5 shows the interactions of the 3-$R_{Ru}$ enantiomer with the active site of GSK-3β. As designed, the imide-NH undergoes hydrogen bonding with the backbone carbonyl of Asp133 and one imide carbonyl group of 3-$R_{Ru}$ undergoes a hydrogen bond with the backbone amide-NH of Val135. A water mediated contact is observed between the carbonyl ligand and the carboxylate of Gln185. This ordered water molecule appears to be unique for GSK-3 and might at least in part be responsible for the observed specificity.

An overlay of the cocrystallized position of staurosporine with the docked binding position of 3 demonstrates how closely ruthenium complex 3 copies the binding mode of staurosporine (FIG. 5). The pyridocarbazole occupies the binding site of the indolocarbazole moiety and the cyclopentadienyl and CO ligand replace the glycosidic ring in the ribose binding site. The ruthenium center is not involved in any direct interactions and serves entirely as an innocent bystander helping to organize the positions of the ligands in the receptor space.

In conclusion, the present novel strategy for the design of ruthenium complexes as protein kinase inhibitors encompasses mimicking the structure of organic indolocarbazoles. Ruthenium complex 3 is by an order of magnitude more potent than staurosporine ($IC_{50}$ of 50 nM against GSK-3α, see blue curve in FIG. 3) and compares well in terms of potency and selectivity with the best published organic GSK-3 inhibitors to date. Such an unprecedented property of an organometallic compound indicates that our approach may lead to a novel class of metallotherapeutics. Replacing natural products with kinetically inert metal complexes may lead to a new class of therapeutics in which a metal center plays the role of an innocent bystander, organizing the orientation of the organic ligands in the receptor space. As an example of this approach, a ruthenium complex is described which copies the binding mode of indolocarbazole protein kinase inhibitors and serves as a reversible, low nanomolar inhibitor for glycogen synthase kinase 3 (GSK-3).

Agents that inhibit GSK3 activity are useful in the treatment of disorders that are mediated by GSK3 activity. In addition, inhibition of GSK3 mimics the activation of growth factor signaling pathways and consequently GSK3 inhibitors are useful in the treatment of diseases in which such pathways are insufficiently active. Examples of diseases that can be treated with GSK3 inhibitors are described below.

Diabetes

Type 2 diabetes is an increasingly prevalent disease of aging. It is initially characterized by decreased sensitivity to insulin and a compensatory elevation in circulating insulin concentrations, the latter of which is required to maintain normal blood glucose levels. Increased insulin levels are caused by increased secretion from the pancreatic beta cells, and the resulting hyperinsulinemia is associated with cardiovascular complications of diabetes. As insulin resistance worsens, the demand on the pancreatic beta cells steadily increases until the pancreas can no longer provide adequate levels of insulin, resulting in elevated levels of glucose in the blood. Ultimately, overt hyperglycemia and hyperlipidemia occur, leading to the devastating long-term complications associated with diabetes, including cardiovascular disease, renal failure and blindness. The exact mechanism(s) causing type 2 diabetes are unknown, but result in impaired glucose transport into skeletal muscle and increased hepatic glucose production, in addition to inadequate insulin response. Dietary modifications are often ineffective, therefore the majority of patients ultimately require pharmaceutical intervention in an effort to prevent and/or slow the progression of the complications of the disease. Many patients can be treated with one or more of the many oral anti-diabetic agents available, including sulfonylureas, to increase insulin secretion. Examples of sulfonylurea drugs include metformin for suppression of hepatic glucose production, and troglitazone, an insulin-sensitizing medication. Despite the utility of these agents, 30-40% of diabetics are not adequately controlled using these medications and require subcutaneous insulin injections. Additionally, each of these therapies has associated side effects. For example, sulfonylureas can cause hypoglycemia and troglitazone can cause severe hepatoxicity. Presently, there is a need for new and improved drugs for the treatment of prediabetic and diabetic patients.

As described above, GSK3 inhibition stimulates insulin-dependent processes and is consequently useful in the treatment of type 2 diabetes. Recent data obtained using lithium salts provides evidence for this notion. The lithium ion has recently been reported to inhibit GSK3 activity. Klein et al., PNAS 93:8455-9 (1996). Since 1924, lithium has been reported to have antidiabetic effects including the ability to reduce plasma glucose levels, increase glycogen uptake, potentiate insulin, up-regulate glucose synthase activity and to stimulate glycogen synthesis in skin, muscle and fat cells. However, lithium has not been widely accepted for use in the inhibition of GSK3 activity, possibly because of its documented effects on molecular targets other than GSK3. The purine analog 5-iodotubercidin, also a GSK3 inhibitor, likewise stimulates glycogen synthesis and antagonizes inactivation of glycogen synthase by glucagon and vasopressin in rat liver cells. Fluckiger-Isler et al., Biochem J 292:85-91 (1993); and Massillon et al., Biochem J 299:123-8 (1994). However, this compound has also been shown to inhibit other serine/threonine and tyrosine kinases. Massillon et al., Biochem J 299:123-8 (1994).

Alzheimer's Disease

GSK3 is also involved in biological pathways relating to Alzheimer's disease (AD). The characteristic pathological features of AD are extracellular plaques of an abnormally processed form of the amyloid precursor protein (APP), so called β-amyloid peptide (β-AP) and the development of intracellular neurofibrillary tangles containing paired helical filaments (PHF) that consist largely of hyperphosphorylated tau protein. GSK3 is one of a number of kinases that have been found to phosphorylate tau protein in vitro on the abnormal sites characteristic of PHF tau, and is the only kinase also demonstrated to do this in living cells and in animals. Lovestone et al., Current Biology 4:1077-86 (1994); and Brownlees et al., Neuroreport 8: 3251-3255 (1997). Furthermore, the GSK3 kinase inhibitor, LiCl, blocks tau hyperphosphorylation in cells. Stambolic et al., Current Biology 6:1664-8 (1996). Thus GSK3 activity may contribute to the generation of neurofibrillary tangles and consequently to disease progression. Recently it has been shown that GSK3β associates with another key protein in AD pathogenesis, presenillin 1 (PS1). Takashima et., PNAS 95:9637-9641 (1998). Mutations in the PS1 gene lead to increased production of β-AP, but the authors also demonstrate that the mutant PS1 proteins bind more tightly to GSK3β and potentiate the phosphorylation of tau, which is bound to the same region of PS1.

Interestingly it has also been shown that another GSK3 substrate, β-catenin, binds to PS1. Zhong et al., Nature 395: 698-702 (1998). Cytosolic β-catenin is targeted for degradation upon phosphorylation by GSK3 and reduced β-catenin activity is associated with increased sensitivity of neuronal cells to β-AP induced neuronal apoptosis. Consequently, increased association of GSK3β with mutant PS1 may account for the reduced levels of β-catenin that have been observed in the brains of PS1-mutant AD patients and to the disease related increase in neuronal cell-death. Consistent with these observations, it has been shown that injection of GSK3 antisense but not sense, blocks the pathological effects of β-AP on neurons in vitro, resulting in a 24 hr delay in the onset of cell death and increased cell survival at 1 hr from 12 to 35%. Takashima et al., PNAS 90:7789-93. (1993). In these latter studies, the effects on cell-death are preceded (within 3-6 hours of β-AP administration) by a doubling of intracellular GSK3 activity, suggesting that in addition to genetic mechanisms that increase the proximity of GSK3 to its substrates, β-AP may actually increase GSK3 activity. Further evidence for a role for GSK3 in AD is provided by the observation that the protein expression level (but, in this case, not specific activity) of GSK3 is increased by 50% in postsynaptosomal supernatants of AD vs. normal brain tissue. Pei et al., J Neuropathol Exp 56:70-78 (1997). Thus, it is believed that specific inhibitors of GSK3 will act to slow the progression of Alzheimer's Disease.

Other CNS Disorders

In addition to the effects of lithium described above, there is a long history of the use of lithium to treat bipolar disorder (manic depressive syndrome). This clinical response to lithium may reflect an involvement of GSK3 activity in the etiology of bipolar disorder, in which case GSK3 inhibitors could be relevant to that indication. In support of this notion it was recently shown that valproate, another drug commonly used in the treatment of bipolar disorder, is also a GSK3 inhibitor. Chen et al., J. Neurochemistry 72:1327-1330 (1999). One mechanism by which lithium and other GSK3 inhibitors may act to treat bipolar disorder is to increase the survival of neurons subjected to aberrantly high levels of excitation induced by the neurotransmitter, glutamate. Nonaka et al., PNAS 95: 2642-2647 (1998). Glutamate-induced neuronal excitotoxicity is also believed to be a major cause of neurodegeneration associated with acute damage, such as in cerebral ischemia, traumatic brain injury and bacterial infection. Furthermore it is believed that excessive glutamate signaling is a factor in the chronic neuronal damage seen in diseases such as Alzheimer's, Huntingdon's, Parkinson's, AIDS associated dementia, amyotrophic lateral sclerosis (AML) and multiple sclerosis (MS). Thomas, J. Am. Geriatr. Soc. 43: 1279-89 (1995). Consequently GSK3 inhibitors are believed to be a useful treatment in these and other neurodegenerative disorders.

Immune Potentiation

GSK3 phosphorylates transcription factor NF-AT and promotes its export from the nucleus, in opposition to the effect of calcineurin. Beals et al., Science 275:1930-33 (1997). Thus, GSK3 blocks early immune response gene activation via NF-AT, and GSK3 inhibitors may tend to permit or prolong activation of immune responses. Thus GSK3 inhibitors are believed to prolong and potentiate the immunostimulatory effects of certain cytokines, and such an effect may enhance the potential of those cytokines for tumor immunotherapy or indeed for immunotherapy in general.

Other Disorders

Lithium also has other biological effects. It is a potent stimulator of hematopoiesis, both in vitro and in vivo. Hammond et al., Blood 55: 26-28 (1980). In dogs, lithium carbonate eliminated recurrent neutropenia and normalized other blood cell counts. Doukas et al. Exp Hematol 14: 215-221 (1986). If these effects of lithium are mediated through the inhibition of GSK3, then GSK3-specific inhibitors may have even broader therapeutic applications.

The Compounds of Chemical Formula I

A compound of chemical formula I comprises

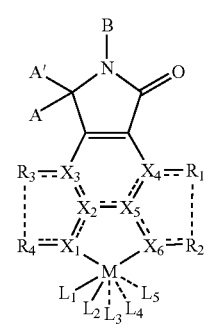

I or a pharmaceutically acceptable salt, ester, or solvate thereof, wherein each $X_1$, $X_2$, $X_3$, $X_4$, $X_5$ and $X_6$, independently, comprises N, C, S, O, B or Si;

each $R_1$, $R_2$, $R_3$ and $R_4$, independently, comprises 1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, ($C_1$-$C_9$)alkoxy, ($C_2$-$C_9$)alkenyloxy, ($C_3$-$C_8$)cycloalkyl, ($C_5$-$C_7$)cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched ($C_1$-$C_9$)alkyl, straight or branched ($C_1$-$C_9$)alkyl substituted with one or more halo, trifluoromethyl, nitro, straight or branched ($C_1$-$C_6$)alkyl, straight or branched ($C_2$-$C_6$)alkenyl, hydroxy, ($C_1$-$C_4$)alkoxy, ($C_2$-$C_4$)alkenyloxy, phenoxy, benzyloxy, amino, or aryl (Ar), O—(($C_1$-$C_9$)alkyl), which may be straight or branched, straight or branched ($C_2$-$C_9$)alkenyl or alkynyl, and straight or branched ($C_2$-$C_9$)alkenyl or alkynyl substituted with one or more halo, trifluoromethyl, nitro, straight or branched ($C_1$-$C_6$)alkyl, straight or branched ($C_2$-$C_6$)alkenyl, hydroxy, ($C_1$-$C_4$)alkoxy, ($C_2$-$C_4$)alkenyloxy, phenoxy, benzyloxy, amino, or Ar, O—(($C_2$-$C_9$)alkenyl), which may be straight or branched, or Ar, and/or $R^1$ and $R_2$, which taken together form a mono-, bi- or tricyclic, carbo- or heterocyclic substituted or unsubstituted ring, wherein when the ring is monocyclic it comprises a 5 to 7 atom ring, when bicyclic or tricyclic it comprises a 3 to 8 atom ring, and when heterocyclic it comprises 1 to 5 O, N and/or S heteroatomic ring, and/or $R_3$ and $R_4$, which taken together form a mono-, bi- or tricyclic, carbo- or heterocyclic substituted or unsubstituted ring, wherein when the ring is monocyclic it comprises a 5 to 7 member ring, when bicyclic or tricyclic it comprises a 3 to 8 member ring, and when heterocyclic it comprises a 1-5 O, N and/or S heteroatomic ring;

Ar comprises a mono-, bi- or tricyclic, carbo- or heterocyclic ring that may be either unsubstituted or substituted in one or more position(s) with halo, hydroxyl, nitro, trifluoromethyl, straight or branched ($C_1$-$C_6$)alkyl or alkenyl, ($C_1$-$C_4$) alkoxy, ($C_1$-$C_4$)alkenyloxy, phenoxy, benzyloxy, or amino; wherein when the ring is a monocyclic ring it comprises a 5-7 membered ring, when a bicyclic or tricyclic ring it comprises a 3-8 membered ring, and when heterocyclic it comprises a 1-5 O, N and/or S heteroatomic ring;

M comprises Ru, Pt, Tc, Re, Os, Rh, Ir, Pd, Au, Cu or any other metal or half-metal;

each A and A', independently, comprises hydrogen, hydroxy, hydroxymethyl, straight or branched ($C_1$-$C_6$) chain alkyl, straight or branched ($C_2$-$C_6$)alkenyl, O-(straight or branched ($C_1$-$C_6$)alkyl), and O-(straight or branched ($C_2$-$C_6$) alkenyl), or A and A' are taken together as =O;

B is hydrogen or $C_1$-$C_6$ straight or branched chain alkyl; and each $L_1$ to $L_n$, independently, comprise a monodentate ligand capable of acting as a ligand for M, and/or $L_1$ and $L_2$, taken together, comprise a bidentate ligand capable of acting as a ligand for M, and/or $L_1$, $L_2$ and $L_3$, taken together, comprise a tridentate ligand capable of acting as a ligand for M, and/or $L_1$, $L_2$, $L_3$ and $L_4$, taken together, comprise a tetradentate ligand capable of acting as a ligand for M; and n comprises a 2, 3, 4 or 5 integer.

In an alternate embodiment of the invention, each $L_1$ to $L_n$, individually as a monodentate ligand, or taken together as a bidentate, tridentate, or tetradentate ligand, comprises one or more of —C≡O, substituted or unsubstituted cyclopentadienyls, 2,2'-bipyridines, 8-hydroxyquinolines, α-aminomethylpyridines, catechols, ortho-phenylenediamines, triazacyclononane, trithianonane, amino acids, halo, hydroxy, carbonyl, amine, nitro, sulfhydryl, pyridine, thiolate, histidine, methionine, cysteine, dimethylsulfoxide, substituted or unsubstituted pyridines, substituted or unsubstituted amines, substituted or unsubstituted diamines, substituted or unsubstituted thiols, substituted or unsubstituted dithiols, substituted or unsubstituted imidazoles, substituted or unsubstituted pyrazoles, substituted or unsubstituted benzimidazoles, substituted or unsubstituted 1,4-dienes, substituted or unsubstituted 2-(aminomethyl)pyridines, substituted or unsubstituted 2-iminopyridines, substituted bipyridines, substituted or unsubstituted phenanthrolines, substituted or unsubstituted 8-hydroxyquinolines, substituted or unsubstituted 6-mercaptopurines and/or substituted or unsubstituted phosphines.

In a further embodiment each $X_1$, $X_2$, $X_3$, $X_4$, $X_5$ and $X_6$, independently, comprises N or C. In another aspect of the inventive subject matter, M comprises Ru or Pt. In another aspect of the invention $R_1$ and $R_2$, taken together, form a monocyclic 5 or 6 membered ring, or a bicyclic indene, indene derivative, naphthalene, or naphthalene derivative ring, which may comprise a carbocyclic or heterocyclic ring, and wherein the ring is substituted with one or more substituents selected from the group consisting of halo, hydroxyl, nitro, trifluoromethyl, $C_1$-$C_6$ straight or branched chain alkyl or alkenyl, $C_1$-$C_4$ alkoxy, $C_1$-$C_4$ alkenyloxy, phenoxy, benzyloxy, and amino. In a preferred embodiment, the indene or naphthalene derivative refers to a fully unsaturated, partially unsaturated, or fully saturated ring structure having the same number of ring atoms as the base indene or naphthalene ring. By way of non-limiting example, an indene derivative includes indole, benzimidazole, indazole, and the like. In yet another aspect of the inventive subject matter, $R_3$ and $R_4$, taken together, form a monocyclic 5 or 6 membered carbocyclic or heterocyclic ring, or a bicyclic indene, indene derivative, naphthalene, or naphthalene derivative carbocyclic or heterocyclic ring.

In an alternate embodiment of the invention, the compound of the invention comprises the chemical formula

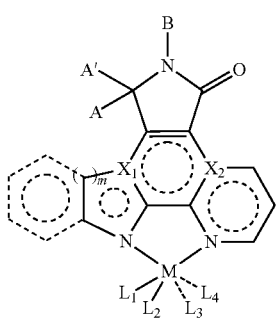

II or a pharmaceutically acceptable salt, ester, or solvate thereof, wherein

A comprises H, A' comprises H, or A and A' taken together are =O;

B comprises hydrogen or straight or branched $C_1$-$C_6$ alkyl;

$X_1$ comprises N or CH;

$X_2$ comprises N or CH;

m comprises 1 or 2;

M comprises Ru or Pt; and each $L_1$, $L_2$, $L_3$ and $L_4$, independently, comprises a monodentate ligand capable of acting as a ligand for M, and/or $L_1$ and $L_2$, taken together, form a bidentate ligand capable of acting as a ligand for M, and/or $L_3$ and $L_4$, taken together, form a bidentate ligand capable of acting as a ligand for M.

In a preferred embodiment, at least one of $X_1$ and $X_2$ comprises N. In another preferred embodiment, each of $X_1$ and $X_2$ comprises CH. In a further preferred embodiment, m is 1. In another embodiment, the monodentate ligand comprises halo, hydroxy, carbonyl, amine, nitro, sulfhydryl, pyridine, thiolate, histidine, methionine, cysteine or dimethylsulfoxide. In a more preferred embodiment, the bidentate ligand comprises bidentate ligand comprises —C≡O, substituted or unsubstituted cyclopentadienyls, 2,2'-bipyridines, 8-hydroxyquinolines, α-aminomethylpyridines, catechols, ortho-phenylenediamines, triazacyclononane, trithianonane, amino acids, substituted or unsubstituted pyridines, amines, diamines, thiols, dithiols, imidazoles, pyrazoles, benzimidazoles, 1,4-dienes, 2-(aminomethyl)pyridines, 2-iminopyridines, substituted bipyridines, phenanthrolines, or 6-mercaptopurines.

In another more preferred embodiment, A and A' taken together are =O; B comprises hydrogen or methyl; $X_1$ comprises CH; $X_2$ comprises CH; m comprises 1 or 2; M comprises Ru; and $L_1$ and $L_2$, taken together, form a bidentate ligand capable of acting as a ligand for the metal M, and $L_3$ and $L_4$, taken together, form a bidentate ligand capable of acting as a ligand for the metal M, wherein each bidentate ligand, independently, comprises unsubstituted or substituted cyclopentadienyl, 2,2'-bipyridine, 8-hydroxyquinoline, α-aminomethylpyridine, catechol, ortho-phenylenediamine, triazacyclononane, or trithianonane, an amino acid, or —C≡O.

In another more preferred embodiment, B comprises hydrogen; m comprises 1; $R_1$ and $R_2$ are taken together to form a pyridine ring; $R_3$ and $R_4$ are taken together to form an unsubstituted indole ring or an indole ring substituted with one or more halo or hydroxy substituents; $L_1$ and $L_2$, taken together, comprise —C≡O; and $L_3$ and $L_4$, taken together, comprise unsubstituted cyclopentadienyl or cyclopentadienyl substituted with methoxycarbonyl.

In yet another more preferred embodiment, the compound of the invention comprises the chemical formula

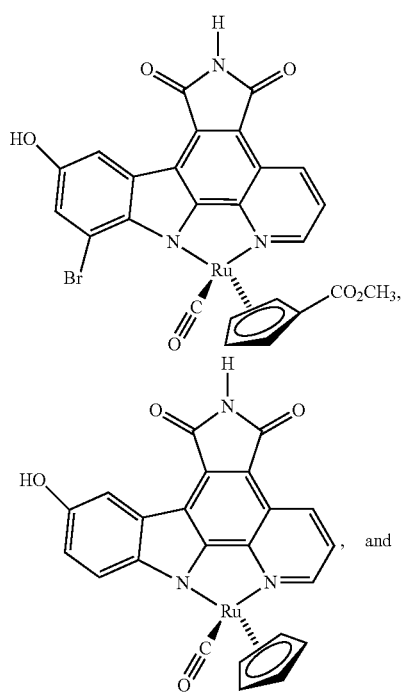

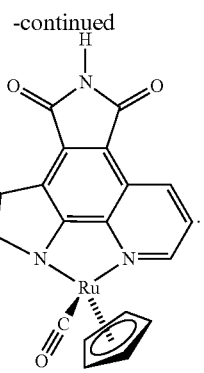

In one most preferred embodiment, the compound comprises the chemical formula

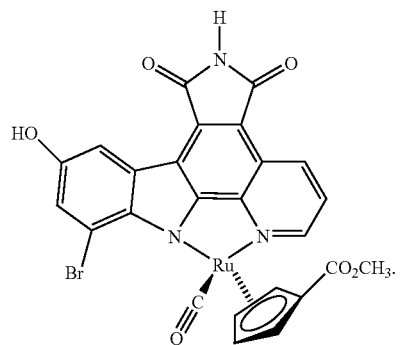

In another most preferred embodiment, the compound comprises the chemical formula

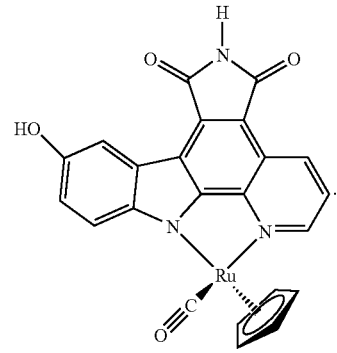

METHODS OF THE INVENTION

The present invention also provides a method for modulating glycogen synthase kinase 3 activity in a subject in need thereof, which comprises administering to the subject (human or animal) an effective amount of a compound of the chemical formula

I

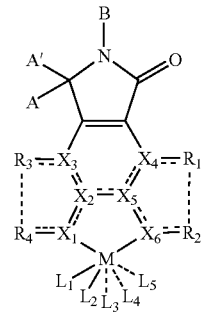

or a pharmaceutically acceptable salt, ester, or solvate thereof, wherein each $X_1$, $X_2$, $X_3$, $X_4$, $X_5$ and $X_6$, independently, comprises N, C, S, O, B or Si;

each $R_1$, $R_2$, $R_3$ and $R_4$, independently, comprises 1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, $(C_1-C_9)$alkoxy, $(C_2-C_9)$alkenyloxy, $(C_3-C_8)$cycloalkyl, $(C_5-C_7)$cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched $(C_1-C_9)$alkyl, straight or branched $(C_1-C_9)$alkyl substituted with one or more halo, trifluoromethyl, nitro, straight or branched $(C_1-C_6)$alkyl, straight or branched $(C_2-C_6)$alkenyl, hydroxy, $(C_1-C_4)$alkoxy, $(C_2-C_4)$alkenyloxy, phenoxy, benzyloxy, amino, or aryl (Ar), O—$((C_1-C_9)$alkyl), which may be straight or branched, straight or branched $(C_2-C_9)$alkenyl or alkynyl, and straight or branched $(C_2-C_9)$alkenyl or alkynyl substituted with one or more halo, trifluoromethyl, nitro, straight or branched $(C_1-C_6)$alkyl, straight or branched $(C_2-C_6)$alkenyl, hydroxy, $(C_1-C_4)$alkoxy, $(C_2-C_4)$alkenyloxy, phenoxy, benzyloxy, amino, or Ar, O—$((C_2-C_9)$alkenyl), which may be straight or branched, or Ar, and/or $R^1$ and $R_2$, which taken together form a mono-, bi- or tricyclic, carbo- or heterocyclic substituted or unsubstituted ring, wherein when the ring is monocyclic it comprises a 5 to 7 atom ring, when bicyclic or tricyclic it comprises a 3 to 8 atom ring, and when heterocyclic it comprises 1 to 5 O, N and/or S heteroatomic ring, and/or $R_3$ and $R_4$, which taken together form a mono-, bi- or tricyclic, carbo- or heterocyclic substituted or unsubstituted ring, wherein when the ring is monocyclic it comprises a 5 to 7 member ring, when bicyclic or tricyclic it comprises a 3 to 8 member ring, and when heterocyclic it comprises a 1-5 O, N and/or S heteroatomic ring;

Ar comprises a mono-, bi- or tricyclic, carbo- or heterocyclic ring that may be either unsubstituted or substituted in one or more position(s) with halo, hydroxyl, nitro, trifluoromethyl, straight or branched $(C_1-C_6)$alkyl or alkenyl, $(C_1-C_4)$ alkoxy, $(C_1-C_4)$alkenyloxy, phenoxy, benzyloxy, or amino; wherein when the ring is a monocyclic ring it comprises a 5-7 membered ring, when a bicyclic or tricyclic ring it comprises a 3-8 membered ring, and when heterocyclic it comprises a 1-5 O, N and/or S heteroatomic ring;

M comprises Ru, Pt, Tc, Re, Os, Rh, Ir, Pd, Au, Cu or any other metal or half-metal;

each A and A', independently, comprises hydrogen, hydroxy, hydroxymethyl, straight or branched $(C_1-C_6)$ chain alkyl, straight or branched $(C_2-C_6)$alkenyl, O-(straight or branched $(C_1-C_6)$alkyl), and O-(straight or branched $(C_2-C_6)$ alkenyl), or A and A' are taken together as =O;

B is hydrogen or $C_1-C_6$ straight or branched chain alkyl; and each $L_1$ to $L_n$, independently, comprise a monodentate ligand capable of acting as a ligand for M, and/or $L_1$ and $L_2$, taken together, comprise a bidentate ligand capable of acting as a ligand for M, and/or $L_1$, $L_2$ and $L_3$, taken together, comprise a tridentate ligand capable of acting as a ligand for M, and/or $L_1$, $L_2$, $L_3$ and $L_4$, taken together, comprise a tetradentate ligand capable of acting as a ligand for M; and n comprises a 2, 3, 4 or 5 integer.

Pharmaceutical Compositions

The present invention also relates to a pharmaceutical composition comprising (i) a therapeutically effective amount of the compound of the chemical formula

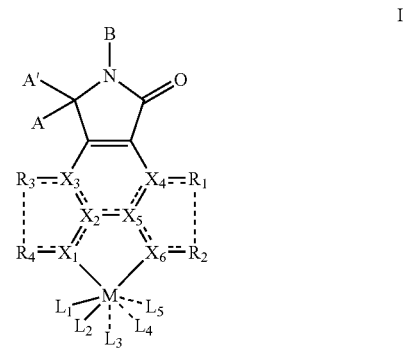

I or a pharmaceutically acceptable salt, ester, or solvate thereof, wherein each $X_1$, $X_2$, $X_3$, $X_4$, $X_5$ and $X_6$, independently, comprises N, C, S, O, B or Si;

each $R_1$, $R_2$, $R_3$ and $R_4$, independently, comprises 1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, $(C_1-C_9)$alkoxy, $(C_2-C_9)$alkenyloxy, $(C_3-C_8)$cycloalkyl, $(C_5-C_7)$cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched $(C_1-C_9)$alkyl, straight or branched $(C_1-C_9)$alkyl substituted with one or more halo, trifluoromethyl, nitro, straight or branched $(C_1-C_6)$alkyl, straight or branched $(C_2-C_6)$alkenyl, hydroxy, $(C_1-C_4)$alkoxy, $(C_2-C_4)$alkenyloxy, phenoxy, benzyloxy, amino, or aryl (Ar), O—$((C_1-C_9)$alkyl), which may be straight or branched, straight or branched $(C_2-C_9)$alkenyl or alkynyl, and straight or branched $(C_2-C_9)$alkenyl or alkynyl substituted with one or more halo, trifluoromethyl, nitro, straight or branched $(C_1-C_6)$alkyl, straight or branched $(C_2-C_6)$alkenyl, hydroxy, $(C_1-C_4)$alkoxy, $(C_2-C_4)$alkenyloxy, phenoxy, benzyloxy, amino, or Ar, O—$((C_2-C_9)$alkenyl), which may be straight or branched, or Ar, and/or $R_1$ and $R_2$, which taken together form a mono-, bi- or tricyclic, carbo- or heterocyclic substituted or unsubstituted ring, wherein when the ring is monocyclic it comprises a 5 to 7 atom ring, when bicyclic or tricyclic it comprises a 3 to 8 atom ring, and when heterocyclic it comprises 1 to 5 O, N and/or S heteroatomic ring, and/or $R_3$ and $R_4$, which taken together form a mono-, bi- or tricyclic, carbo- or heterocyclic substituted or unsubstituted ring, wherein when the ring is monocyclic it comprises a 5 to 7 member ring, when bicyclic or tricyclic it comprises a 3 to 8 member ring, and when heterocyclic it comprises a 1-5 O, N and/or S heteroatomic ring;

Ar comprises a mono-, bi- or tricyclic, carbo- or heterocyclic ring that may be either unsubstituted or substituted in one or more position(s) with halo, hydroxyl, nitro, trifluoromethyl, straight or branched $(C_1-C_6)$alkyl or alkenyl, $(C_1-C_4)$ alkoxy, $(C_1-C_4)$alkenyloxy, phenoxy, benzyloxy, or amino; wherein when the ring is a monocyclic ring it comprises a 5-7 membered ring, when a bicyclic or tricyclic ring it comprises a 3-8 membered ring, and when heterocyclic it comprises a 1-5 O, N and/or S heteroatomic ring;

M comprises Ru, Pt, Tc, Re, Os, Rh, Ir, Pd, Au, Cu or any other metal or half-metal;

each A and A', independently, comprises hydrogen, hydroxy, hydroxymethyl, straight or branched ($C_1$-$C_6$) chain alkyl, straight or branched ($C_2$-$C_6$)alkenyl, O-(straight or branched ($C_1$-$C_6$)alkyl), and O-(straight or branched ($C_2$-$C_6$) alkenyl), or A and A' are taken together as =O;

B is hydrogen or $C_1$-$C_6$ straight or branched chain alkyl; and each $L_1$ to $L_n$, independently, comprise a monodentate ligand capable of acting as a ligand for M, and/or $L_1$ and $L_2$, taken together, comprise a bidentate ligand capable of acting as a ligand for M, and/or $L_1$, $L_2$ and $L_3$, taken together, comprise a tridentate ligand capable of acting as a ligand for M, and/or $L_1$, $L_2$, $L_3$ and $L_4$, taken together, comprise a tetradentate ligand capable of acting as a ligand for M; and n comprises a 2, 3, 4 or 5 integer; and (ii) a pharmaceutically acceptable carrier.

In one embodiment, the novel pharmaceutical composition of the invention comprises a therapeutically effective amount of the active agent indicated above. This effective amount will generally comprise from about 0.1 mg to about 100 mg of the active agent per kilogram of patient body Weight per day. This effective amount may vary depending upon the physical status of the patient and other factors well known in the art. Moreover, it will be understood that this dosage of active agent may be administered in a single or multiple dosage units to provide the desired therapeutic effect. If desired, other therapeutic agents may be employed in conjunction with those provided by the present invention.

The compounds of the invention are preferably delivered to the patient as a composition also comprising a pharmaceutically acceptable carrier. Such carriers are well known in the art and generally will be in either solid or liquid form. Solid form pharmaceutical preparations which may be prepared according to the present inventive subject matter include powders, tablets, dispersible granules, capsules, cachets and suppositories. Although other forms are also contemplated. In general, solid form preparations will comprise from about 5% to about 90% by weight of the active agent. A solid carrier may be comprised of one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art. For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid pharmaceutical preparations may comprise up to 100% by weight of the subject active agent. .

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of the liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the invention may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition. Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition. Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition. Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition. Colorants useful in the present inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884, which text is accordingly incorporated herein by reference. Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition. Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

The compounds of the present invention are not expected to display significant adverse interactions with other synthetic or naturally occurring substances. Thus, a compound of the present inventive subject matter may be administered in combination with other glycogen synthase kinase 3 inhibitor compounds and compositions, compounds and compositions useful for treating diseases and disorders mediated by glycogen synthase kinase 3 activity, including by way of example and without limitation diseases and disorders such as diabetes, Alzheimer's disease and other neurodegenerative disorders, obesity, atherosclerotic cardiovascular disease, essential hypertension, polycystic ovary syndrome, syndrome X, ischemia, traumatic brain injury, bipolar disorder, immunodeficiency, and cancer. In particular the compounds of the present invention may be administered in combination with such other compounds and compositions.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the present therapeutic agents of the inventive subject matter.

Synthesis of Inventive Compounds

The compounds of the present invention may be readily prepared by standard techniques of organic chemistry, utilizing the general synthetic pathways described herein, particularly in the "Supplementary Material" appended hereto. In the preparation of the compounds of the inventive subject matter, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the present inventive subject matter. The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

Route(s) of Administration

The route(s) of administration of the compounds and compositions of the present inventive subject matter are well known to those skilled in the art. See, for example, "Remington's Pharmaceutical Sciences", 18th Edition, Chapter 86, pp. 1581-1592, Mack Publishing Company (1990). The compounds and compositions may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intramuscular, intraperitoneally, intrathecally, intraventricularly, intrasternal, and intracranial injection or infusion techniques. To be effective therapeutically as central nervous system targets, the compounds and compositions should readily penetrate the blood-brain barrier when peripherally administered. Compounds which cannot penetrate the blood-brain barrier can be effectively administered by an intraventricular route.

The compounds and compositions may be administered in the form of sterile injectable preparations, for example, as sterile injectable aqueous or oleaginous suspensions. These suspensions, may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, in one preferred embodiment, the compounds and compositions may be administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

The compounds may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax, and polyethylene glycols.

Furthermore, the compounds may be administered topically, especially when the conditions addressed for treatment involve areas or organs readily accessible by topical application, including the lower intestinal tract. Suitable topical formulations can be readily prepared for such areas or organs. For example, topical application to the lower intestinal tract can be effected in a rectal suppository formulations (see above) or in suitable enema formulations.

It is envisioned that the continuous administration or sustained delivery of the compounds and compositions of the present inventive subject matter may be advantageous for a given condition. While continuous administration may be accomplished via a mechanical means, such as with an infusion pump, it is contemplated that other modes of continuous or near continuous administration may be practiced. For example, such administration may be by subcutaneous or muscular injections as well as oral pills.

Techniques for formulating a variety of other sustained- or controlled-delivery means, such as liposome carriers, bioerodible particles or beads and depot injections, are also known to those skilled in the art.

Dosage

Dosage levels on the order of about 0.001 mg to about 100 mg per kilogram body weight of the active ingredient compounds or compositions are useful in the treatment of the above conditions, with preferred levels ranging from 200 mg per day to 1600 mg per day. However, other dosages are also contemplated. The compounds and compositions of the present inventive subject matter may usually be given in two or three doses daily. Starting with a low dose (200-300 mg) twice daily and slowly working up to higher doses if needed is a preferred strategy. The amount of active ingredient that may be combined with the carrier materials to produce a single dosage form will vary depending upon the host treated and the particular mode of administration. It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the present inventive subject matter and are not intended to be limitations thereon. Unless otherwise indicated, all percentages are based upon 100% by weight of the final composition.

Example 1

Preparation of Inventive Compounds

The following are examples illustrating the preparation of preferred active agents provided according to the present inventive subject matter. NMR spectra were recorded on a Bruker AM-500 (500 MHz) spectrometer. Low-resolution mass spectra were obtained on an LC platform from Micromass using ESI technique. High-resolution mass spectra were obtained with a Micromass AutoSpec instrument using either CI or ES ionization. Infrared spectra were recorded on a Perkin Elmer 1600 series FTIR spectrometer. Solvents and reagents were used as supplied from Aldrich or ACROS. Shown in Scheme 1 below is the synthetic scheme for pyridocarbazoles 4 and ruthenium complex 3.

Scheme 1

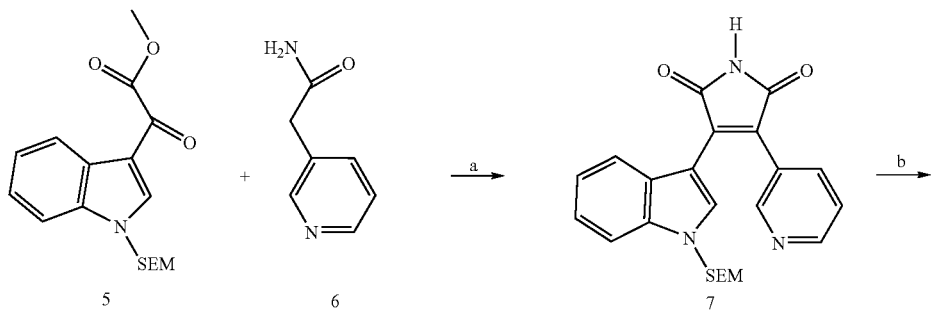

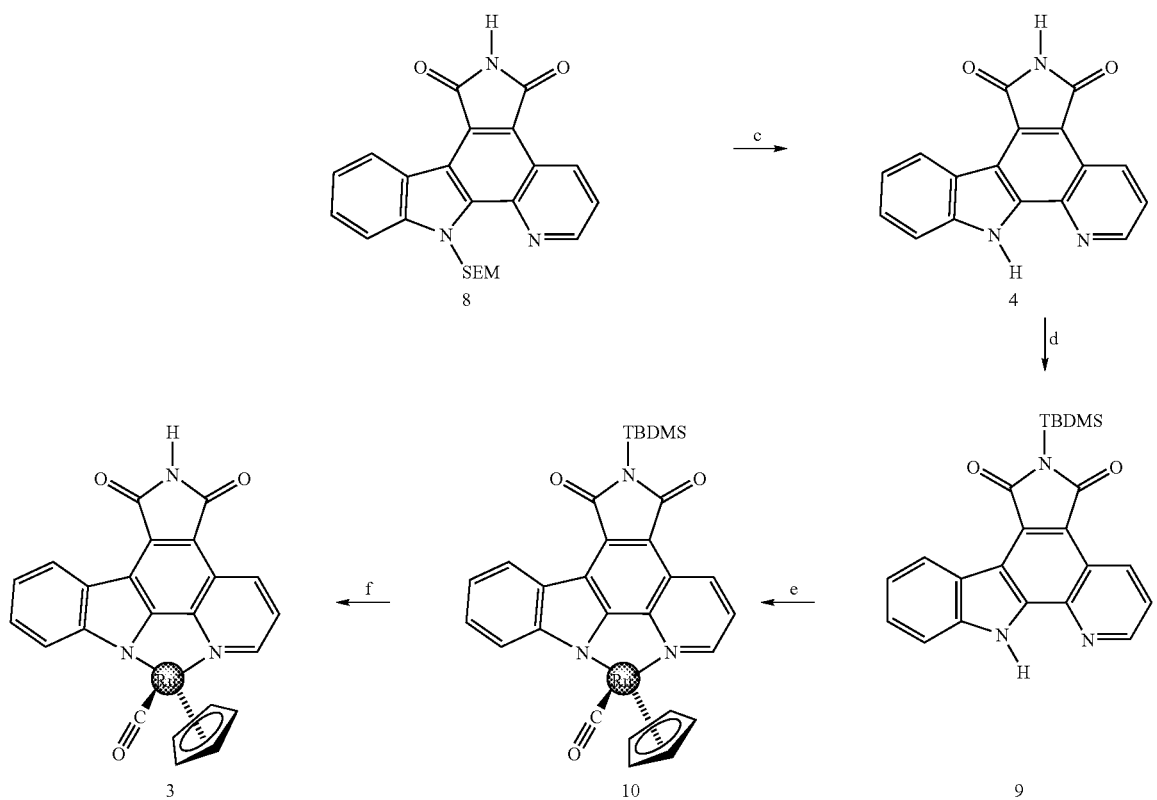

Reaction conditions and reagents are indicated according to the following key: (a) 3 equivalents of KOtBu, DMF, 4 Å mol. sieves (50%). (b) Photolysis in MeCN with a medium-pressure mercury lamp in presence of air and catalytic amounts of $I_2$ (63%). (c) $LiBF_4$, $MeCN/H_2O$, reflux (100%). (d) Reflux in MeCN with tert-butyldimethylsilyloxy-methoxyethene, (92.5%). (e) $[CpRu(CO)(MeCN)_2]^+PF_6^-$, 1 equiv of $K_2CO_3$, overnight in MeCN at 55° C. (87%). (f) TBAF, $CH_2Cl_2$ (96%). $SEM=CH_2OCH_2CH_2Si(CH_3)_3$.

Scheme 2 below shows the synthetic scheme for the methylated ruthenium complex 3Me. Reaction conditions and reagents are indicated according to the following key: (a) KOtBu (1.5 equiv.), $CH_3I$ (5 equiv.), DMF (91%). (b) $LiBF_4$ (10 equiv.), $CH_3CN/H_2O$ (95%). (c) $[CpRu(CO)(MeCN)_2]^+$ $PF_6^-$, $K_2CO_3$ (1 equiv.), overnight in MeCN at 55° C. (96%).

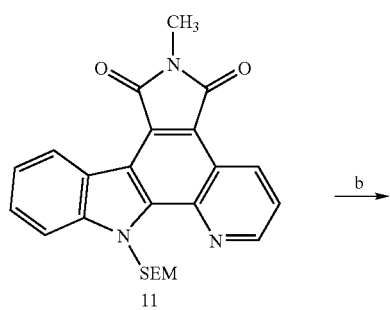

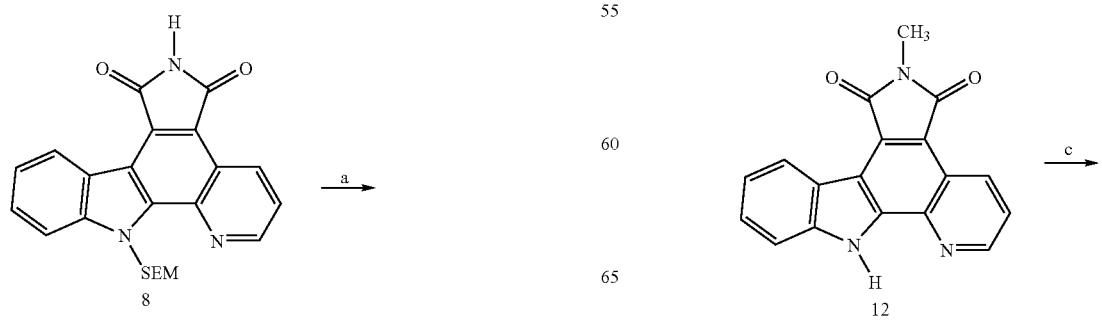

-continued

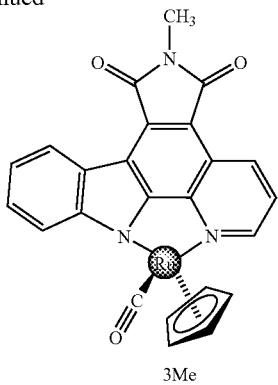

3Me

Synthesis of Compound 7

To a stirred solution of 5[1] (6.82 g, 20.45 mmol) and pyridine 3-acetamide 6[2] (2.53 g, 18.59 mmol) in DMF (50 ml) at 0° C. a solution of potassium tert-butoxide (6.26 g, 55.77 mmol) in DMF (50 ml) was added dropwise. The solution was stirred at 0° C. and was allowed to warm to room temperature overnight. The resulting dark red solution was cooled to 0° C. and 20% aqueous ammonium chloride (300 ml) was carefully added. This mixture was extracted with ethyl acetate three times, and the organic layer was dried with $MgSO_4$ and concentrated. After being dried under vacuum to remove residual DMF, the residue was subjected to silica gel column chromatography with ethyl acetate/hexane (2:1) as the eluting solvent. The resulting orange-yellow condensation product 7 was isolated in modest yield (3.88 g, 50%). $^1$H-NMR (500 MHz, $CDCl_3$) δ (ppm) 8.74 (dd, J=2.2, 0.5 Hz, 1H), 8.58 (dd, J=4.9, 1.7 Hz, 1H), 8.41 (br s, 1H), 8.05 (s, 1H), 7.86 (dt, J=8.0, 1.9 Hz, 1H), 7.50 (d, J=8.2 Hz, 1H), 7.28 (ddd, J=8.1, 5.1, 0.6 Hz, 1H), 7.19 (td, J=7.7, 1.0 Hz, 1H), 6.86 (td, J=7.6, 1.0 Hz, 1H), 6.41 (d, J=8.1 Hz, 1H), 5.55 (s, 2H), 3.57 (t, J=8.1 Hz, 2H), 0.93 (t, J=8.1 Hz, 2H), −0.04 (s, 9H). $^{13}$C-NMR (125 MHz, $CDCl_3$) δ (ppm) 171.0, 170.9, 150.7, 149.9, 137.2, 134.2, 133.8, 126.8, 126.7, 125.0, 123.7, 123.3, 122.2, 121.9, 111.2, 105.1, 97.8, 76.5, 66.7, 17.9, −1.2. IR (thin film) ν ($cm^{-1}$)=3585, 3471, 3266, 3200, 3056, 2922, 2712, 1979, 1712, 1624, 1513, 1468, 1396, 1337, 1238, 1178, 1078, 838. HRMS calcd for $C_{23}H_{26}N_3O_3Si$ ($MH^+$) 420.17435, found ($MH+$) 420.1761.

Synthesis of Compound 8

A stirred solution of 7 (1.0 g, 2.39 mmol) in acetonitrile (200 ml) with catalytic amounts of iodine (10 mol %, 0.239 mmol, 60.7 mg) was irradiated with a medium pressure lamp for 2.5 hours while air was bubbled through the solution. The resulting suspension was evaporated, and the reaction repeated three times with this scale. The crude reaction mixtures were combined and purified by silica gel chromatography (methylene chloride:methanol 20:1). The isolated material was further purified by recrystallization from acetonitrile (300 ml) to yield 8 (2.5 g, 63%). $^1$H-NMR (500 MHz, $CDCl_3$) δ (ppm) 9.41 (dd, J=8.5, 1.5 Hz, 1H), 9.14 (d, J=7.9 Hz, 1H), 9.05 (dd, J=4.0, 1.8 Hz, 1H), 7.81 (d, J=8.2 Hz, 1H), 7.65 (m, 3H), 7.51 (t, J=7.3 Hz, 1H), 6.87 (s, 2H), 3.68 (t, J=7.7 Hz, 2H), 0.92 (t, J=7.8 Hz, 2H), −0.17 (s, 9H). $^{13}$C-NMR (125 MHz, $CDCl_3$) δ (ppm) 169.6, 168.7, 150.0, 142.0, 140.0, 139.0, 134.0, 128.6, 127.9, 125.5, 123.0, 122.61, 122.60, 121.6, 119.6, 117.3, 111.4, 74.4, 66.0, 18.2, −1.3. IR (thin film) ν=3178, 3059, 2925, 2845, 1754, 1701, 1601, 1554, 1521, 1467, 1400, 1340, 1247, 1207, 1180, 1073, 1006, 833 $cm^{-1}$. HRMS calcd for $C_{23}H_{24}N_3O_3Si$ ($MH^+$) 418.1587, found ($MH^+$) 418.1566.

Synthesis of Compound 4

A suspension of SEM-protected pyridocarbazole 8 (2.14 g, 5.1 mmol) and lithium tetrafluoroborate (4.78 g, 51 mmol) in acetonitrile (605 ml) and water (26.7 ml) (22.6:1 ratio) was heated to reflux for 20 hours. The resulting suspension was cooled to room temperature and the volume reduced to about 30 ml. The suspension was cooled to −20° C. for two hours, and the yellow precipitate was isolated via vacuum filtration. The filtrate was washed extensively with water to remove any excess salt. Drying under vacuum afforded free pyridocarbazole 4 (1.47 g, 100%). $^1$H-NMR (500 MHz, DMSO-$d^6$) δ (ppm) 11.26 (s, 1 NH), 9.26 (dd, J=8.5, 1.7 Hz, 1H), 9.14 (dd, J=4.2, 1.5 Hz, 1H), 8.89 (d, J=7.9 Hz, 1H), 7.85 (dd, J=8.5, 4.2 Hz, 1H), 7.77 (d, J=7.7 Hz, 1H), 7.58 (t, J=7.1 Hz, 1H), 7.40 (t, J=7.4 Hz, 1H). IR (KBr) ν ($cm^{-1}$)=3237, 2978, 2755, 1755, 1690, 1531, 1337, 1226, 756, 644.

Synthesis of Compound 9

To a stirred suspension of 4 (1.34 g, 4.7 mmol) in acetonitrile (134 ml) was added tert-butyldimethylsilyloxy-methoxyethene (3.05 ml, 14 mmol). The mixture was refluxed for two hours during which time the yellow suspension became an orange solution. The solution was cooled to room temperature and the solvent evaporated. The crude yellow solid was subjected to silica gel chromatography (ethyl acetate:hexanes 5:1, later 1:1) to yield silyl protected imide 9 as a yellow solid (1.73 g, 92.5%). $^1$H-NMR(500 MHz, $CDCl_3$) δ (ppm) 10.36 (br s, 1 NH), 9.44 (dd, J=8.5, 1.4 Hz, 1H), 9.09 (d, J=8.0 Hz, 1H), 9.01 (dd, J=4.3, 1.5 Hz, 1H), 7.65 (dd, J=8.5, 4.3 Hz, 1H), 7.58 (m, 2H), 7.45 (t, J=8.0 Hz, 1H), 1.09 (s, 9H), 0.66 (s, 6H). $^{13}$C-NMR (125 MHz, $CDCl_3$) δ (ppm) 175.6, 174.5, 150.6, 140.1, 139.7, 138.4, 134.7, 130.9, 127.6, 125.8, 123.1, 122.6, 122.1, 122.0, 121.0, 115.5, 111.7, 26.7, 19.4, −3.7. IR (thin film) ν ($cm^{-1}$)=2927, 2857, 1752, 1690, 1598, 1528, 1462, 1405, 1339, 1308, 1281, 1260, 1233, 1071, 1044.

Synthesis of Compound 10

A yellow suspension of 9 (65 mg, 0.162 mmol), [CpRu(CO)($CH_3CN$)$_2$]$^+$PF6$^-$ (68.2 mg, 0.162 mmol) and potassium carbonate (22.4 mg, 0.162 mmol) in acetonitrile (6.5 ml) was purged with argon for 15 mins, then heated to 55° C overnight.[3] The resulting bright red solution was evaporated and the crude material purified by silica gel chromatography (ethyl acetate:hexanes 1:5, later 1:1) to yield complex 10 as a sticky purple solid (84 mg, 87%). $^1$H-NMR (500 MHz, $CDCl_3$) δ (ppm) 9.27 (dd, J=8.3, 1.0 Hz, 1H), 8.91 (m, 2H), 7.58 (td, J=7.0, 1.2 Hz, 1H), 7.48 (m, 2H), 7.40 (td, J=7.0, 1.0 Hz, 1H), 5.23 (s, 5H), 1.07 (s, 9H), 1.07 (s, 9H), 0.64 (s, 6H). $^{13}$C-NMR (125 MHz, $CDCl_3$) δ (ppm) 199.9 (M-CO), 175.7, 175.2, 155.4, 154.5, 153.4, 145.3, 134.6, 133.3, 126.2, 125.4, 124.4, 122.1, 120.1, 115.8, 115.3, 114.4, 80.8 (M-Cp), 29.9, 26.7, 19.4, −3.7. IR (thin film) ν ($cm^{-1}$)=2919, 1954 (s, M-CO), 1725, 1690, 1584, 1414, 1337, 1279, 1126, 1049, 826.

Synthesis of Compound 3

To a stirred solution of 10 (76 mg, 0.128 mmol) in $CH_2Cl_2$ (5 ml) at room temperature, TBAF (1M in tetrahydrofuran) (0.192 ml, 0.192 mmol) was added. The solution was stirred for 10 minutes at room temperature, after which time glacial acetic acid (11 μl, 0.192 mmol) was added. After stirring for ten minutes at room temperature, the solvent was evaporated and the crude material purified by silica gel chromatography (ethyl acetate:hexanes 1:10, later 1:1) to yield 3 as a purple solid (59 mg, 96%). $^1$H-NMR (500 MHz, $CDCl_3$) δ (ppm) 9.22 (d, J=8.3 Hz, 1H), 8.95 (d, J=5.0 Hz, 1H), 8.87 (d, J=7.9 Hz, 1H), 7.61 (t, J=7.8 Hz, 1H), 7.51 (m, 2H), 7.44 (t, J=7.4 Hz, 1H), 7.40 (br s, 1H), 5.25 (s, 5H). $^{13}$C-NMR (125 MHz, $CDCl_3$/$CD_3OD$) δ (ppm) 199.6, 171.3, 170.9, 155.4, 154.6, 153.4, 144.7, 133.8, 131.5, 126.3, 124.9, 124.0, 122.2, 122.1, 119.9, 116.0, 115.3, 112.0, 80.6. IR (thin film) ν (cm$^{-1}$)= 2929, 1949 (s, M-CO), 1751, 1696, 1522, 1418, 1343, 1230.

Synthesis of Compound 11

To a yellow solution of 8 (100 mg, 0.024 mmol) in 5 ml DMF was added potassium tert-butoxide (40 mg, 0.036 mmol). The resulting red solution was stirred for 15 mins after which time iodomethane was added (7.5 µl, 0.12 mmol). The yellow solution was stirred for another 15 minutes and, after TLC analysis, the reaction was quenched by the addition of 20% aqueous ammonium acetate. The mixture was extracted three times with methylene chloride, dried with MgSO$_4$, and dried under vacuum. The resulting crude material was subjected to silica gel chromatography (ethyl acetate:hexanes 1:5) to yield 11 as a yellow solid (94 mg, 91%). $^1$H-NMR (500 MHz, CDCl$_3$) δ (ppm) 9.38 (dd, J=8.5, 1.8 Hz, 1H), 9.12 (dt, J=8.0, 0.8 Hz, 1H), 9.00 (dd, J=4.2, 1.8 Hz, 1H), 7.76 (d, J=8.3 Hz, 1H), 7.63 (td, J=7.6, 1.2 Hz, 1H), 7.59 (dd, J=8.5, 4.2 Hz, 1H), 7.48 (td, J=7.6, 1.0 Hz, 1H), 6.79 (s, 2H), 3.65 (t, J=8.2 Hz, 2H), 3.27 (s, 3H), 0.90 (t, J=8.2 Hz, 2H), −0.19 (s, 9H). $^{13}$C-NMR (125 MHz, CDCl$_3$) δ (ppm) 170.0, 169.2, 149.7, 141.9, 139.6, 138.5, 133.7, 128.0, 127.7, 125.4, 122.7, 122.44, 122.41, 121.6, 119.0, 117.1, 111.2, 74.3, 65.9, 24.0, 18.2, −1.3. IR (thin film) ν (cm$^{-1}$)=2921, 1757, 1704, 1594, 1556, 1522, 1470, 1441, 1398, 1374, 1336, 1250, 1207, 1130, 1072, 1010, 991, 929, 905, 838, 795, 757, 747, 690. LRMS calcd for C$_{24}$H$_{25}$N$_3$O$_3$Si (M+Na)$^+$ 454.1563, found (M+Na)$^+$ 454.2932.

Synthesis of Compound 12

A suspension of SEM-protected pyridocarbazole 11 (100 mg, 0.231 mmol) and lithium tetrafluoroborate (216 mg, 2.31 mmol) in acetonitrile (28 ml) and water (1.2 ml) was heated to reflux for twenty hours. The resulting suspension was cooled to room temperature and the volume was reduced to about 3 ml. The suspension was cooled to −20° C. for two hours, and the yellow precipitate was isolated via vacuum filtration. The filtrate was washed extensively with water to remove any excess salt. Drying under vacuum afforded free pyridocarbazole 12 (66 mg, 95%). $^1$H-NMR (500 MHz, DMSO-d$^6$) δ (ppm) 9.14 (d, J=8.3 Hz, 1H), 9.07 (d, J=4.1 Hz, 1H), 8.81 (d, J=7.9 Hz, 1H), 7.77 (dd, J=8.4, 4.2 Hz, 1H), 7.73 (d, J=8.1 Hz, 1H), 7.56 (t, J=7.8 Hz, 1H), 7.38 (t, J=7.6 Hz, 1H), 3.08 (s, 3H). IR (thin film) ν (cm$^{-1}$)=3331, 1754, 1691, 1594, 1459, 1387, 1329, 1252, 1102, 1073, 1020, 996, 745. HRMS calcd for C$_{18}$H$_{11}$N$_3$O$_2$ (MH$^+$) 302.09295, found (MH$^+$) 302.09362.

Synthesis of Compound 3Me

A suspension of 12 (9.5 mg, 0.032 mmol), potassium carbonate (4.4 mg, 0.032 mmol), and [CpRu(CO)(CH$_3$CN)$_2$]$^+$ PF6$^-$ (13.3 mg, 0.032 mmol) in acetonitrile (0.95 ml) was purged with argon for 15 minutes, then refluxed overnight.$^3$ The resulting red solution was evaporated and subjected to silica gel chromatography, first with ethyl acetate:hexanes 1:1, then with methylene chloride:methanol 10:1. The product was eluted as a bright purple solid (15 mg, 96%). $^1$H-NMR (500 MHz, CDCl$_3$) δ (ppm) 9.21 (d,J=8.3 Hz, 1H), 8.90 (m, 2H), 7.60 (t, J=8.1 Hz, 1H), 7.50 (m, 2H), 7.43 (t, J=7.45 Hz, 1H), 5.25 (s, 5H), 3.28 (s, 3H). $^{13}$C-NMR (125 MHz, CDCl$_3$) δ (ppm) 199.8, 170.5, 170.1, 155.4, 154.4, 153.6, 144.7, 134.1, 131.1, 126.5, 125.3, 124.3, 122.23, 122.19, 120.2, 116.4, 115.4, 111.6, 80.8, 24.0. IR (thin film) ν (cm$^{-1}$)=2932, 2856, 1937(s, M-CO), 1746, 1694, 1579, 1522, 1498, 1412, 1379, 1327, 1269, 1227, 1136, 1079, 821, 788. HRMS calcd for C$_{24}$H$_{15}$N$_3$O$_3$Ru (M$^+$) 495.01568, found (M$^+$) 495.0155.

References Related to the Synthesis of the Inventive Compounds

The following references are considered relevant to an understanding of the syntetic examples, and their inclusion for such purpose is not an admission that such documents are material to patentability of the claimed subject matter, nor an admission that such documents are prior art. The relevant texts of the following references are incorporated herein by reference. Documents considered material to patentability will be separately identified by Information Disclosure Statement. 1) Piers, E.; Britton, R.; Anderson, R. J. *J. Org. Chem.* 2000, 65, 530-535. 2) Pyridine-3-acetamide was prepared by partial hydrolysis of commercially available pyridine-3-acetonitrile with concentrated sulfuric acid. 3) Gill, T. P.; Mann, K. R. *Organometallics.* 1982, 1, 485-488.

Separation of the Enantiomers of Compound 3

Figure 6:
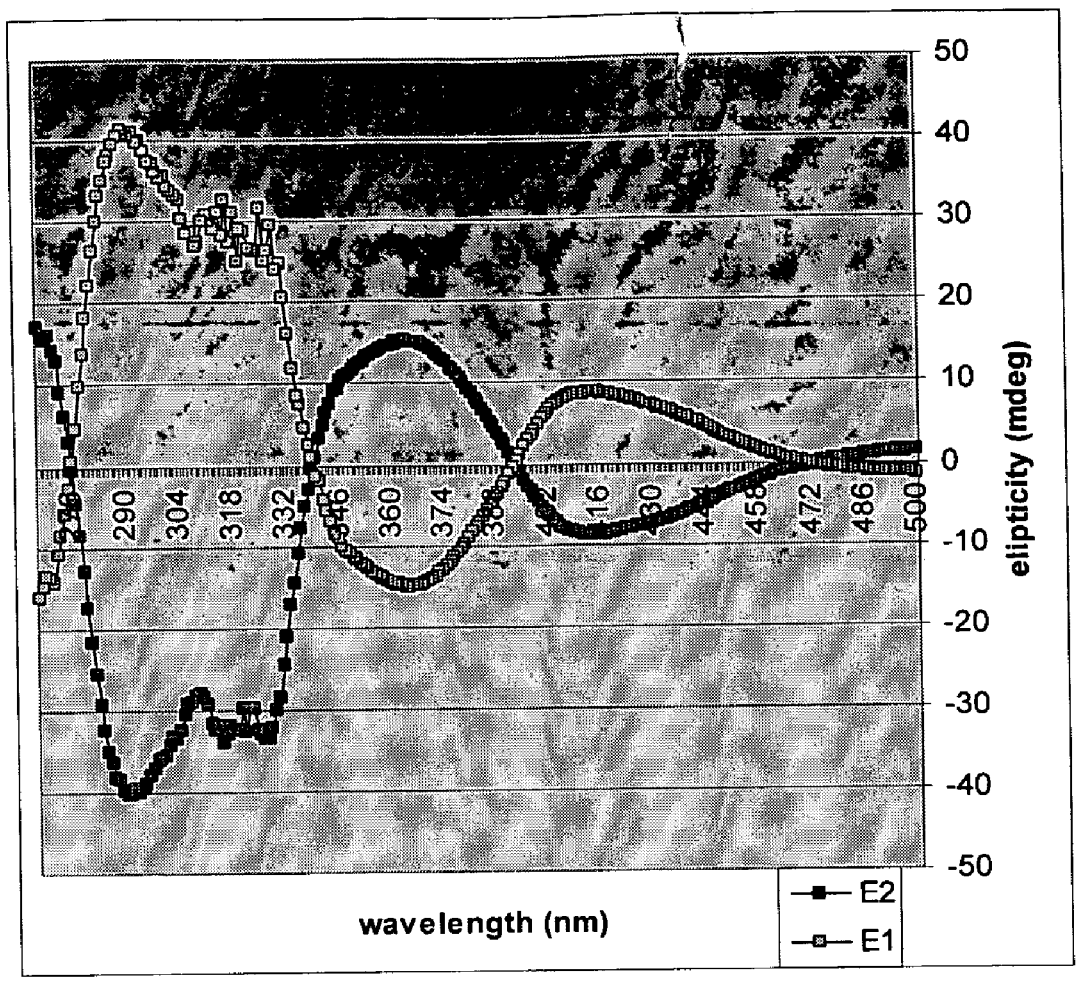
FIG. 6 depicts circular dichroism spectra of the two enantiomers of compound 3.

Enantiomers were separated using a ChiralPak AD-H analytical HPLC column (Daicel/Chiral Technologies) using a gradient of hexanes:ethanol (7:3) to hexanes:ethanol (1:4) in twenty minutes with a flow rate of 0.95 ml/minute. The enantiomers were baseline separated under these conditions. The enantiomers did not show any significant racemization in an acetonitrile solution over a time period of 12 hours. The circular dichroism spectra of the separated enantiomers is shown in FIG. 6 and were recorded on an AVIV Model 62ADS spectrometer. Elipticities were multiplied by a correction factor to correct for any concentration discrepancies.

Example 2

GSK-3 and Protein Kinase Inhibition

The following examples illustrate the potency of the inventive compositions against GSK-3 and other protein kinases. Protein kinases and substrates were purchased from Upstate Biotechnology USA, except for poly(Glu-Tyr 4:1) which was obtained from Sigma-Aldrich.

Assays for Abl (Human), CHK1 (Human), GSK-3α (Human), GSK-3β (Human), Lck (Human) RSK1 (Rat), and ZAP-70 (Human)

Various concentrations of inhibitor were incubated at room temperature in 20 mM MOPS, 30 mM MgCl$_2$, 0.8 µg/µl BSA, 5% DMSO (resulting from the inhibitor stock solution), pH 7.0, in presence of substrate (phospho-glycogen synthase peptide-2 for GSK-3:20 µM, abltide for Abl:25 µM, MAP-KAP kinase 2 substrate peptide for RSK1: 50 µM, CHK1 substrate peptide for CHK1: 0.2 µg/ul, Src peptide for Lck: 50 µM, poly(Glu-Tyr 4:1) for ZAP-70: 0.1 mg/ml) and kinase (GSK, Abl: 0.4 ng/µl), RSK1 (0.04 ng/µl), CHK1 (1.33 ng/µl), Lck (0.8 ng/µl), ZAP-70 (5.33 ng/µl). After 15 mins, the reaction was initiated by adding ATP to a final concentration of 20 µM, including approximately 0.04 µCi/µl [γ-$^{32}$P] ATP. Reactions were performed in a total volume of 25 µl. After 30 min, the reaction was terminated by spotting 17.5 µl on a circular P81 phosphocellulose paper (diameter 2.1 cm, Whatman) followed by washing four times (five minutes each wash) with 0.75% phosphoric acid and once with acetone. The dried P81 papers were transferred to a scintillation vial and 5 ml of scintillation cocktail were added and the counts per minute (CPM) determined with a Beckmann 6000 scintillation counter. IC$_{50}$ values were defined to be the concentration of inhibitor at which the CPM was 50% of the control sample, corrected by the background.

Assays for MAPK1/Erk1 (Human)

Procedure as above, but in 30 mM Tris-HCl, 20 mM MgCl$_2$, 0.8 µg/µl BSA, 5% DMSO (resulting from the inhibitor stock solution), pH 7.5, in presence of myelin basic protein (2 µg/ul) and MAPK1 (0.4 ng/µl).

Assay for c-Src (Human)

Procedure as above, but in 40 mM Tris-HCl, 32.5 mM MgCl$_2$, 2.5 mM MnCl$_2$, 0.2 mM EGTA, 0.025 mM sodium orthovanadate, 0.2 mM dithiothreitol, 0.8 μg/μl BSA, 5% DMSO (resulting from the inhibitor stock solution), pH 7.5, in presence of c-Src substrate peptide (50 μM) and c-Src kinase (0.1 u/μl).

Assay for PKCα (Human)

Procedure as above, but in 10 mM HEPES, 0.025% Triton X-100, 10 mM $MgCl_2$, 0.3 mM $CaCl_2$, 0.1 mg/ml phosphatidylserine, 0.01 mg/ml diacylglycerol, 5 mM β-glycerophosphate, 0.2 mM sodium orthovanadate, 0.8 μg/μl BSA, 5% DMSO (resulting from the inhibitor stock solution), pH 7.5, in presence of histone H1 (0.05 mg/ml) and PKCα (0.4 ng/μl).

Lineweaver-Burk Kinetics

Various concentrations of ATP and inhibitor 3 were incubated at room temperature for one hour in 20 mM MOPS, 30 mM $MgCl_2$, 0.8 μg/μl BSA, 5% DMSO (resulting from the inhibitor stock solution), pH 7.0, in presence of phosphoglycogen synthase peptide 2 (0.06 mg/ml) and glycogen synthase kinase 3α (human, active, 0.4 ng/μl). The total reaction volume was 25 μl. Each ATP solution contained the same ratio of ATP to radioactive [γ-$^{32}$P]ATP and were as follow: 500 μM ATP with 0.18 μCi/μl [γ-$^{32}$P]ATP, 20 μM ATP with 7.27 nCi/μl [γ-$^{32}$P]ATP, 10 μM ATP with 3.64 nCi/μl [γ-$^{32}$P]ATP, 5 μM ATP with 1.82 nCi/μl [γ-$^{32}$P]ATP, and 2.5 μM ATP with 0.91 nCi/μl [γ-$^{32}$P]ATP. The inhibitor concentrations used were 0 nM, 1 nM, 2 nM, 4 nM and 8 nM. Prior to the addition of ATP, the inhibitor 3, substrate and protein kinase were preincubated for 15 minutes in the reaction buffer. After one hour, the reactions were stopped by spotting 17.5 μl of the reaction solution on a circular P81 phosphocellulose paper (diameter 2.1 cm, Whatman) followed by washing four times (five minutes each wash) with 0.75% phosphoric acid and once with acetone. After the papers dried, they were transferred to scintillation vials and 5 ml of scintillation cocktail were added. The counts per minute (CPM) were measured with a Beckmann 6000 scintillation counter. CPM values were treated as relative initial velocities. All reactions were performed at least in duplicate. The inhibition constant ($K_i$) of 3 was calculated by nonlinear regression using the software GraphPad Prism (Version 4.0).

X-Ray Structure Determination

Crystals were grown by dissolving the N-benzylated derivative of 3 (3Bn) in $CHCl_3/CH_3CN$ (~1:1), the solution was filtered through cotton and was allowed to evaporate slowly. Compound 3Bn, $C_{31}H_{20}N_3O_3Cl_3Ru$, crystallizes in the orthorhombic space group Pbca (systematic absences hk0: h=odd, 0k1: k=odd, and h01: 1=odd) with a=11.6076(5) Å, b=17.6809(7) Å, c=27.2021(11) Å, V=5582.8(4) Å$^3$, Z=8 and $d_{calc}$=1.642 g/cm$^3$. X-ray intensity data were collected on a Rigaku Mercury CCD area detector employing graphite-monochromated Mo-K$_□$ radiation ($□$=0.71069 Å) at a temperature of 143° K. Preliminary indexing was performed from a series of twelve 0.5° rotation images with exposures of 30 seconds. A total of 440 rotation images were collected with a crystal to detector distance of 36 mm, a 2$□$ swing angle of −12°, rotation widths of 0.5° and exposures of 60 seconds: scan no. 1 was a φ-scan from 60° to 240° at ω=0° and χ=0° and scan no. 2 was an ω-scan from −20° to 20° at χ=−90° and φ=0°. Rotation images were processed using CrystalClear[i], producing a listing of unaveraged F$^2$ and $□(F^2)$ values which were then passed to the CrystalStructure[ii] program package for further processing and structure solution on a Dell Pentium III computer. A total of 31748 reflections were measured over the ranges 5.16 $□$ 2 $□$ 54.96°, −15 $□$ h $□$ 13, −22 $□$ k $□$ 19, −34 $□$ l $□$ 35 yielding 6323 unique reflections ($R_{int}$=0.0218).

The intensity data were corrected for Lorentz and polarization effects and for absorption using REQAB[iii] (minimum and maximum transmission 0.844, 1.000).

[i]. CrystalClear: Rigaku Corporation, 1999.
[ii]. CrystalStructure: Crystal Structure Analysis Package, Rigaku Corp. Rigaku/MSC (2002).
[iii]. REQAB4: R. A. Jacobsen, (1994). Private Communication.

The structure was solved by direct methods (SIR97[iv]). Refinement was by full-matrix least squares based on F$^2$ using SHELXL-97[v].

[iv]. SIR97: A. Altomare, M. Burla, M. Camalli, G. Cascarano, C. Giacovazzo, A. Guagliardi, A. Moliterni, G. Polidori & R. Spagna (1999). *J. Appl. Cryst.*, 32, 115-119.
[v]. SHELXL-97: Program for the Refinement of Crystal Structures, G. M. Sheldrick (1997), University of Göttingen, Germany.

All reflections were used during refinement (F$^2$'s that were experimentally negative were replaced by F$^2$=0). The weighting scheme used was w=1/[$□^2$($F_o^2$)+0.0649P$^2$+12.6077P] where P=($F_o^2$+2$F_c^2$)/3. Non-hydrogen atoms were refined anisotropically and hydrogen atoms were refined using a "riding", model. Refinement converged to $R_1$=0.0461 and $wR_2$=0.1225 for 5718 reflections for which F>4$□$(F) and $R_1$=0.0508, $wR_2$=0.1278 and GOF=1.042 for all 6323 unique, non-zero reflections and 371 variables[vi]. The maximum $□/□$ in the final cycle of least squares was 0.002 and the two most prominent peaks in the final difference Fourier were +1.224 and −1.569 e/Å$^3$.

[vi]. $R_1=\Sigma||F_o|-|F_c||/\Sigma|F_o| wR_2=\{\Sigma(F_o^2-F_c^2)^2/\Sigma w(F_o^2)^2\}^{1/2}$ GOF=$\{\Sigma w(F_o^2-F_c^2)^2/(n-p)\}^{1/2}$ where n=the number of reflections and p=the number of parameters refined.

Figure 7:
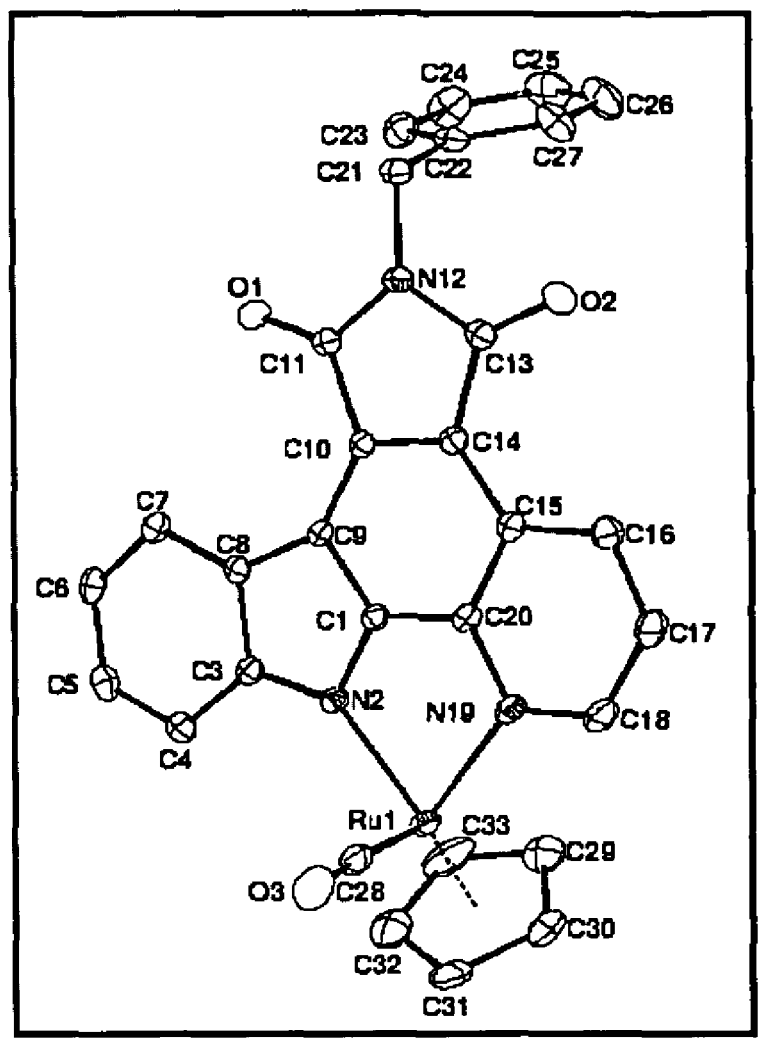
FIG. 7 depicts an ORTEP drawing of compound 3Bn with 30% probability thermal ellipsoids.

Table 1 lists cell information, data collection parameters, and refinement data. Tables 2 and 3 list bond distances and bond angles. FIG. 7 is an ORTEP[vii] representation of the molecule with 30% probability thermal ellipsoids displayed.

[vii]. "ORTEP-II: A Fortran Thermal Ellipsoid Plot Program for Crystal Structure Illustrations". C. K. Johnson (1976) ORNL-5138.

TABLE 1

| Summary of Structure Determination of Compound 3Bn | |
|---|---|
| Formula | $C_{31}H_{20}N_3O_3Cl_3Ru$ |
| Formula weight: | 689.92 |
| Crystal class: | orthorhombic |
| Space group: | Pbca (#61) |
| Z | 8 |
| Cell constants: | |
| a | 11.6076(5)Å |
| b | 17.6809(7)Å |
| c | 27.2021(11)Å |
| V | 5582.8(4)Å$^3$ |
| $□$ | 8.88 cm$^{-1}$ |
| crystal size, mm | 0.42 × 0.35 × 0.27 |
| $D_{calc}$ | 1.642 g/cm$^3$ |
| F(000) | 2768 |
| Radiation: | Mo—K$_□$($□$ = 0.71069Å) |
| 2$□$ range | 5.16–54.96° |
| hkl collected: | −15$□$h$□$13; −22$□$k$□$19; −34$□$l$□$35 |
| No. reflections measured: | 31748 |
| No. unique reflections: | 6323 ($R_{int}$ = 0.0218) |
| No. observed reflections | 5718 (F > 4$□$) |
| No. reflections used in refinement | 6323 |
| No. parameters | 371 |
| R indices (F > 4$□$ | $R_1$ = 0.0461 |
| | $wR_2$ = 0.1225 |
| R indices (all data | $R_1$ = 0.0508 |
| | $wR_2$ = 0.1278 |
| GOF: | 1.042 |
| Final Difference Peaks, e/Å$^3$ | +1.224, −1.569 |

TABLE 2

Bond Distances in Compound 3Bn (Å)

| | | | | | |
|---|---|---|---|---|---|
| Ru1-C28 | 1.860(3) | Ru1-N2 | 2.106(2) | Ru1-N19 | 2.132(3) |
| Ru1-C31 | 2.169(3) | Ru1-C30 | 2.183(4) | Ru1-C32 | 2.188(4) |
| Ru1-C33 | 2.235(4) | Ru1-C29 | 2.242(4) | N2-C1 | 1.342(4) |
| N2-C3 | 1.387(4) | N12-C11 | 1.395(4) | N12-C13 | 1.399(4) |
| N12-C21 | 1.461(4) | N19-C18 | 1.337(4) | N19-C20 | 1.362(4) |
| C1-C20 | 1.403(4) | C1-C9 | 1.415(4) | C3-C4 | 1.398(4) |
| C3-C8 | 1.432(4) | C4-C5 | 1.383(5) | C5-C6 | 1.402(5) |
| C6-C7 | 1.384(4) | C7-C8 | 1.399(4) | C8-C9 | 1.439(4) |
| C9-C10 | 1.398(4) | C10-C14 | 1.393(4) | C10-C11 | 1.497(4) |
| C11-O1 | 1.206(4) | C13-O2 | 1.216(4) | C13-C14 | 1.469(4) |
| C14-C15 | 1.427(4) | C15-C20 | 1.408(4) | C15-C16 | 1.409(4) |
| C16-C17 | 1.378(5) | C17-C18 | 1.402(5) | C21-C22 | 1.510(4) |
| C22-C23 | 1.378(5) | C22-C27 | 1.387(5) | C23-C24 | 1.388(5) |
| C24-C25 | 1.373(6) | C25-C26 | 1.380(7) | C26-C27 | 1.388(5) |
| C28-O3 | 1.148(4) | C29-C33 | 1.411(7) | C29-C30 | 1.433(6) |
| C30-C31 | 1.399(6) | C31-C32 | 1.410(6) | C32-C33 | 1.415(7) |
| C34-C13 | 1.691(6) | C34-C11 | 1.745(5) | C34-C12 | 1.766(6) |

TABLE 3

Bond Angles in Compound 3Bn (°)

| | | | | | |
|---|---|---|---|---|---|
| C28-Ru1-N2 | 94.55(11) | C28-Ru1-N19 | 90.78(13) | N2-Ru1-N19 | 78.65(9) |
| C28-Ru1-C31 | 92.6(2) | N2-Ru1-C31 | 144.05(14) | N19-Ru1-C31 | 136.48(14) |
| C28-Ru1-C30 | 111.82(14) | N2-Ru1-C30 | 153.55(13) | N19-Ru1-C30 | 102.19(13) |
| C31-Ru1-C30 | 37.5(2) | C28-Ru1-C32 | 108.8(2) | N2-Ru1-C32 | 107.18(13) |
| N19-Ru1-C32 | 158.68(14) | C31-Ru1-C32 | 37.8(2) | C30-Ru1-C32 | 63.3(2) |
| C28-Ru1-C33 | 146.0(2) | N2-Ru1-C33 | 94.83(12) | N19-Ru1-C33 | 123.2(2) |
| C31-Ru1-C33 | 61.9(2) | C30-Ru1-C33 | 62.2(2) | C32-Ru1-C33 | 37.3(2) |
| C28-Ru1-C29 | 149.6(2) | N2-Ru1-C29 | 115.86(13) | N19-Ru1-C29 | 96.15(14) |
| C31-Ru1-C29 | 62.4(2) | C30-Ru1-C29 | 37.8(2) | C32-Ru1-C29 | 62.7(2) |
| C33-Ru1-C29 | 36.7(2) | C1-N2-C3 | 105.3(2) | C1-N2-Ru1 | 111.4(2) |
| C3-N2-Ru1 | 143.2(2) | C11-N12-C13 | 111.7(2) | C11-N12-C21 | 124.3(2) |
| C13-N12-C21 | 123.9(2) | C18-N19-C20 | 117.2(3) | C18-N19-Ru1 | 129.7(2) |
| C20-N19-Ru1 | 113.1(2) | N2-C1-C20 | 121.5(3) | N2-C1-C9 | 114.2(2) |
| C20-C1-C9 | 124.2(3) | N2-C3-C4 | 128.3(3) | N2-C3-C8 | 110.7(2) |
| C4-C3-C8 | 120.9(3) | C5-C4-C3 | 118.0(3) | C4-C5-C6 | 121.4(3) |
| C7-C6-C5 | 121.4(3) | C6-C7-C8 | 118.5(3) | C7-C8-C3 | 119.7(3) |
| C7-C8-C9 | 134.5(3) | C3-C8-C9 | 105.8(2) | C10-C9-C1 | 115.1(2) |
| C10-C9-C8 | 141.0(3) | C1-C9-C8 | 103.9(2) | C14-C10-C9 | 121.9(3) |
| C14-C10-C11 | 107.4(2) | C9-C10-C11 | 130.7(3) | O1-C11-N12 | 125.3(3) |
| O1-C11-C10 | 128.9(3) | N12-C11-C10 | 105.9(2) | O2-C13-N12 | 124.1(3) |
| O2-C13-C14 | 129.5(3) | N12-C13-C14 | 106.4(2) | C10-C14-C15 | 122.9(3) |
| C10-C14-C13 | 108.6(2) | C15-C14-C13 | 128.5(3) | C20-C15-C16 | 116.6(3) |
| C20-C15-C14 | 115.8(2) | C16-C15-C14 | 127.6(3) | C17-C16-C15 | 118.5(3) |
| C16-C17-C18 | 121.2(3) | N19-C18-C17 | 121.8(3) | N19-C20-C1 | 115.2(3) |
| N19-C20-C15 | 124.8(3) | C1-C20-C15 | 120.1(3) | N12-C21-C22 | 111.6(2) |
| C23-C22-C27 | 119.0(3) | C23-C22-C21 | 120.6(3) | C27-C22-C21 | 120.3(3) |
| C22-C23-C24 | 120.6(3) | C25-C24-C23 | 120.0(4) | C24-C25-C26 | 120.0(4) |
| C25-C26-C27 | 119.8(4) | C22-C27-C26 | 120.5(4) | O3-C28-Ru1 | 176.7(3) |
| C33-C29-C30 | 106.8(4) | C33-C29-Ru1 | 71.4(2) | C30-C29-Ru1 | 68.9(2) |
| C31-C30-C29 | 107.7(4) | C31-C30-Ru1 | 70.7(2) | C29-C30-Ru1 | 73.4(2) |
| C30-C31-C32 | 109.5(4) | C30-C31-Ru1 | 71.8(2) | C32-C31-Ru1 | 71.9(2) |
| C31-C32-C33 | 106.7(4) | C31-C32-Ru1 | 70.4(2) | C33-C32-Ru1 | 73.2(2) |
| C29-C33-C32 | 109.3(4) | C29-C33-Ru1 | 71.9(2) | C32-C33-Ru1 | 69.5(2) |
| C13-C34-C11 | 114.1(3) | C13-C34-C12 | 110.1(3) | C11-C34-C12 | 110.5(3) |

REFERENCES

The following references are considered relevant to an understanding of the inventive subject matter, and their inclusion for such purpose is not an admission that such documents are material to patentability of the claimed subject matter, nor an admission that such documents are prior art. The relevant texts of the following references are incorporated herein by reference. Documents considered material to patentability will be separately identified by Information Disclosure Statement.

(1) Metal-based drugs: (a) Orvig, C.; Abrams, M. J. (Eds.) Chem. Rev. 1999, 99, 2201-2842. (b) Guo, Z.; Sadler, P. J. Angew. Chem. Int. Ed. 1999, 38, 1512-1531. (c) Farrell, N. (Ed.) Coord. Chem. Rev. 2002, 232, 1-230.

(2) Metal complexes as enzyme inhibitors: Louie, A. Y.; Meade, T. J. Chem. Rev. 1999, 99, 2711-2734. (3) For pioneering work, see: (a) Dwyer, F. P.; Gyarfas, E. C.; Rogers, W. P.; Koch, J. H. Nature 1952, 170, 190-191. (b) Dwyer, F. P.; Gyarfas, E. C.; Wright, R. D.; Shulman, A. Nature 1957, 179, 425-426.

(4) Taube, H. Chem. Rev. 1952, 50, 69-126.

(5) Zhang, L.; Carroll, P. J.; Meggers, E. Org. Lett. 2004, 6, 521-523.

(6) Taylor, S. S.; Radzio-Andzelm, E. Curr. Opin. Chem. Biol. 1997, 1, 219-226.

(7) (a) Garcia-Echeverria, C.; Traxler, P.; Evans, D. B. Med. Res. Rev. 2000, 20, 28-57. (b) Bridges, A. J. Chem. Rev. 2001, 101, 2541-2571.

(8) (a) Toledo, L. M.; Lydon, N. B. Structure 1997, 5, 1551-1556. (b) Lawrie, A. M.; Noble, M. E. M.; Tunnah, P.; Brown, N. R.; Johnson, L. N.; Endicott, J. A. Nature Struct. Biol. 1997, 4, 796-801.

(9) A related cycloruthenation of 2-pyridylindoles and 2-pyridylpyrroles has been reported, but no structures were provided: (a) Thummel, R. P.; Hedge, V. J. Org. Chem. 1989, 54, 1720-1725. (b) Wu, F.; Chamchoumis, C. M.; Thummel, R. P. Inorg. Chem. 2000, 39, 584-590.

(10) Brunner, H. Angew. Chem. Int. Ed. 1999, 38, 1194-1208.

(11) Bertrand, J. A.; Thieffine, S.; Vulpetti, A.; Cristiani, C.; Valsasina, B.; Knapp, S.; Kalisz, H. M.; Flocco, M. J. Mol. Biol. 2003, 333, 393-407.

(12) Cohen, P.; Goedert, M. Nature Rev. Drug Discov. 2004, 3, 479-487.

The following references are considered relevant to an understanding of the structure determination examples, and their inclusion for such purpose is not an admission that such documents are material to patentability of the claimed subject matter, nor an admission that such documents are prior art. The relevant texts of the following references are incorporated herein by reference. Documents considered material to patentability will be separately identified by Information Disclosure Statement.

The invention being thus described, it will be obvious that the same may be modified or varied in many ways. Such modifications and variations are not to be regarded as a departure from the spirit and scope of the invention and all such modifications and variations are intended to be included within the scope of the following claims.

We claim:

1. A compound of formula II:

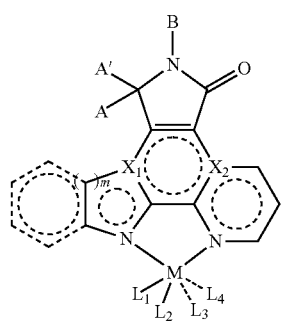

or a pharmaceutically acceptable salt or ester thereof, wherein
A is H and A' is H, or A and A' taken together form =O;
B is hydrogen or straight or branched ($C_1$-$C_6$) alkyl;
$X_3$ is C;
$X_4$ is C;
m is 1 or 2;
M is Ru or Pt; and
each $L_1$, $L_2$, $L_3$ and $L_4$, independently, is a monodentate ligand for M, and/or $L_1$ and $L_2$, taken together, form a bidentate ligand for M, and/or $L_3$ and $L_4$, taken together, form a bidentate ligand for M.

2. A compound selected from the following

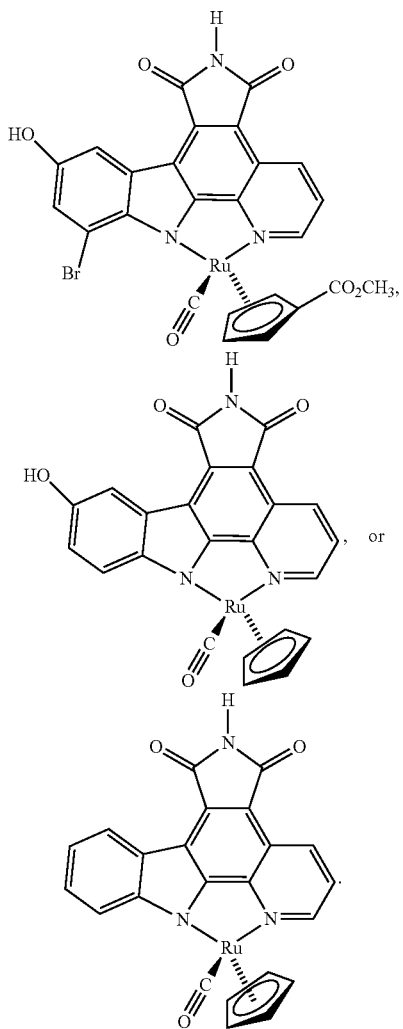

* * * * *

UNITED STATES PATENT AND TRADEMARK OFFICE
CERTIFICATE OF CORRECTION

PATENT NO. : 8,080,660 B2  
APPLICATION NO. : 11/228381  
DATED : December 20, 2011  
INVENTOR(S) : Eric Meggers, Howard Bregman and Douglas S. Williams Page 1 of 1

It is certified that error appears in the above-identified patent and that said Letters Patent is hereby corrected as shown below:

In the Claims

Column 35,

Claim 1, lines 19-31, delete " 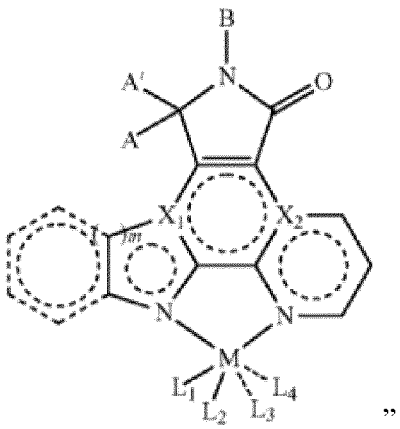 "

and insert -- 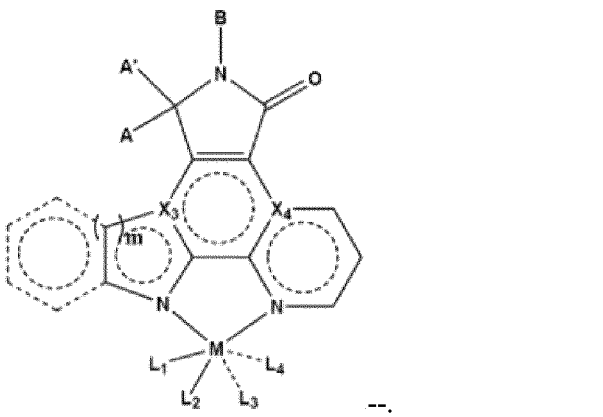 --.

Signed and Sealed this  
Twenty-fourth Day of May, 2016

Michelle K. Lee  
*Director of the United States Patent and Trademark Office*